US007378077B2

(12) United States Patent
Fritzberg et al.

(10) Patent No.: US 7,378,077 B2
(45) Date of Patent: *May 27, 2008

(54) HIGH DOSE RADIONUCLIDE COMPLEXES FOR BONE MARROW SUPPRESSION

(75) Inventors: Alan R. Fritzberg, Olga, WA (US); Lauren Marie Tatalick, Redmond, WA (US); Kent R. Thoelke, Seattle, WA (US); James Kyle Bryan, Seattle, WA (US); Mark D. Hylarides, Stanwood, WA (US); Elizabeth K. John, San Diego, CA (US)

(73) Assignee: Poniard Pharmaceuticals, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/485,183

(22) Filed: Jul. 12, 2006

(65) Prior Publication Data

US 2007/0053833 A1 Mar. 8, 2007

Related U.S. Application Data

(60) Continuation of application No. 10/882,054, filed on Jun. 30, 2004, which is a division of application No. 10/784,476, filed on Feb. 23, 2004, now Pat. No. 7,097,823, which is a continuation of application No. 10/159,245, filed on May 29, 2002, now abandoned, which is a division of application No. 10/014,335, which is a continuation of application No. PCT/US00/16052, filed on Jun. 12, 2000, now Pat. No. 6,767,531.

(60) Provisional application No. 60/149,821, filed on Aug. 19, 1999, provisional application No. 60/143,780, filed on Jul. 13, 1999, provisional application No. 60/139,065, filed on Jun. 11, 1999.

(51) Int. Cl.
*A61K 51/00* (2006.01)
*A61M 36/14* (2006.01)

(52) U.S. Cl. .................. 424/1.65; 424/1.11; 424/9.1; 514/492; 514/836; 534/15

(58) Field of Classification Search ............... 424/1.11, 424/1.37, 1.65, 9.1; 534/15; 514/836, 492
See application file for complete search history.

(56) References Cited

U.S. PATENT DOCUMENTS

| 3,032,584 | A | 5/1962 | Bergel et al. |
| 3,032,585 | A | 5/1962 | Bergel et al. |
| 3,398,198 | A | 8/1968 | Kersnar et al. |
| 3,726,912 | A | 4/1973 | McCrary et al. |
| 3,852,414 | A | 12/1974 | Adler et al. |
| 3,931,396 | A | 1/1976 | Bardy et al. |
| 3,965,254 | A | 6/1976 | Tofe et al. |
| 3,974,268 | A | 8/1976 | Subramanian et al. |
| 3,989,730 | A | 11/1976 | Subramanian et al. |
| 4,017,596 | A | 4/1977 | Loberg et al. |
| 4,058,704 | A | 11/1977 | Shimizu |
| 4,075,314 | A | 2/1978 | Wolfangel et al. |
| 4,104,366 | A | 8/1978 | Schmidt-Dunker et al. |
| 4,187,284 | A | 2/1980 | Rolleston et al. |
| 4,399,817 | A | 8/1983 | Benedict |
| 4,508,625 | A | 4/1985 | Graham |
| 4,515,767 | A | 5/1985 | Simon et al. |
| 4,560,548 | A | 12/1985 | Simon et al. |
| 4,606,907 | A | 8/1986 | Simon et al. |
| 4,639,365 | A | 1/1987 | Sherry |
| 4,647,447 | A | 3/1987 | Gries et al. |
| 4,678,667 | A | 7/1987 | Meares et al. |
| 4,707,353 | A | 11/1987 | Bugaj et al. |
| 4,752,464 | A | 6/1988 | Lieberman et al. |
| 4,808,541 | A | 2/1989 | Mikola et al. |
| 4,853,209 | A | 8/1989 | Kaplan et al. |
| 4,882,142 | A | 11/1989 | Simon et al. |
| 4,885,363 | A | 12/1989 | Tweedle et al. |
| 4,897,254 | A | 1/1990 | Simon et al. |
| 4,897,255 | A | 1/1990 | Fritzberg et al. |
| 4,898,724 | A | 2/1990 | Simon et al. |
| 4,937,333 | A | 6/1990 | Garlich et al. |
| 4,957,939 | A | 9/1990 | Gries et al. |

(Continued)

FOREIGN PATENT DOCUMENTS

CA 1078731 6/1980

(Continued)

OTHER PUBLICATIONS

"Abstract Book, Annual Congress of the EANM", *European Journal of Nuclear Medicine and Molecular Imaging*, 31, Helsinki, 2004, including abstracts P908, P925-P936, and P946-P952,(2004).

"Bone Cancer Therapy Project Funding Awarded to Brookhaven National Laboratory for Diatide-Licensed Product", Distribution: Business Editors and Health/Medical Writers,(1999).

"Breast Cancer; Genitourinary Cancer; Multiple Myeloma", *Annotated Guide to Cancer Chemotherapeutic Regimens 1999/2000*, Oncology Special Edition, 13-14; 17-18; 32.

(Continued)

*Primary Examiner*—Dameron L. Jones
(74) *Attorney, Agent, or Firm*—Schwegman, Lundberg & Woessner, P.A.

(57) ABSTRACT

The present invention relates to a method of suppressing bone marrow (BM) and treating conditions that arise in or near bone such as cancer, myeloproliferative diseases, autoimmune diseases, infectious diseases, metabolic diseases or genetic diseases, with compositions having as their active ingredient a radionuclide complexed with a chelating agent such as macrocyclic aminophosphonic acid.

16 Claims, 4 Drawing Sheets

U.S. PATENT DOCUMENTS

| | | |
|---|---|---|
| 4,976,950 A | 12/1990 | Simon et al. |
| 5,059,412 A | 10/1991 | Simon et al. |
| 5,064,633 A | 11/1991 | Simon et al. |
| 5,066,478 A | 11/1991 | Simon et al. |
| 5,089,249 A | 2/1992 | Fritzberg et al. |
| 5,202,109 A | 4/1993 | Fritzberg et al. |
| 5,286,497 A | 2/1994 | Hendrickson et al. |
| 5,300,279 A | 4/1994 | Simon et al. |
| 5,393,512 A | 2/1995 | Vanderheyden et al. |
| 5,587,451 A | 12/1996 | Athey et al. |
| 5,621,001 A | 4/1997 | Canetta et al. |
| 5,641,803 A | 6/1997 | Canetta et al. |
| 5,665,761 A | 9/1997 | Canetta et al. |
| 5,670,537 A | 9/1997 | Canetta et al. |
| 5,679,318 A | 10/1997 | Vanderheyden et al. |
| 5,707,610 A | 1/1998 | Ibsen et al. |
| 5,708,169 A | 1/1998 | Hester, Jr. et al. |
| 5,712,275 A | 1/1998 | Van Gestel |
| 5,714,467 A | 2/1998 | Boman et al. |
| 5,714,504 A | 2/1998 | Lindberg et al. |
| 5,714,604 A | 2/1998 | Kiefer |
| 5,756,472 A | 5/1998 | Liesch et al. |
| 5,756,505 A | 5/1998 | Nishino et al. |
| 5,756,685 A | 5/1998 | Fritzberg et al. |
| 5,756,725 A | 5/1998 | Wilkening et al. |
| 5,760,063 A | 6/1998 | Lam et al. |
| 5,762,907 A | 6/1998 | Simon et al. |
| 5,770,617 A | 6/1998 | LaVoie et al. |
| 5,773,421 A | 6/1998 | Alder et al. |
| 5,773,443 A | 6/1998 | Ray et al. |
| 5,773,696 A | 6/1998 | Liang et al. |
| 5,783,570 A | 7/1998 | Yokota et al. |
| 5,786,325 A | 7/1998 | Borromeo et al. |
| 5,801,172 A | 9/1998 | Clapp-Shapiro et al. |
| 5,807,854 A | 9/1998 | Bartroli et al. |
| 5,814,634 A | 9/1998 | Nishino et al. |
| 5,824,698 A | 10/1998 | Hasler et al. |
| 5,824,874 A | 10/1998 | Ulbrich et al. |
| 5,830,855 A | 11/1998 | Takemoto |
| 5,830,889 A | 11/1998 | Iwata et al. |
| 5,837,253 A | 11/1998 | Cohen |
| 5,837,726 A | 11/1998 | Liu et al. |
| 5,849,956 A | 12/1998 | Koga et al. |
| 5,854,213 A | 12/1998 | Bouffard |
| 5,854,280 A | 12/1998 | Gomez et al. |
| 5,856,347 A | 1/1999 | Hashiguchi et al. |
| 5,859,032 A | 1/1999 | Nishino et al. |
| 5,861,430 A | 1/1999 | Markonius |
| 5,863,773 A | 1/1999 | Gunawardana et al. |
| 5,866,549 A | 2/1999 | Or et al. |
| 5,872,249 A | 2/1999 | Park et al. |
| 5,876,738 A | 3/1999 | Ohno et al. |
| 5,888,526 A | 3/1999 | Tsubai et al. |
| 5,888,941 A | 3/1999 | Bartroli et al. |
| 5,891,890 A | 4/1999 | Nishino et al. |
| 5,908,862 A | 6/1999 | Wai Lee et al. |
| 5,910,498 A | 6/1999 | Yazaki et al. |
| 5,917,084 A | 6/1999 | Jiang |
| 5,919,438 A | 7/1999 | Saint-Leger |
| 5,919,925 A | 7/1999 | Burton et al. |
| 6,005,083 A | 12/1999 | Kasina |
| 6,177,551 B1 | 1/2001 | Kasina |
| 6,187,910 B1 | 2/2001 | Kasina |
| 6,241,961 B1 | 6/2001 | Benes et al. |
| 6,528,627 B1 | 3/2003 | Kasina |
| 6,767,531 B2 * | 7/2004 | Fritzberg et al. ............ 424/1.65 |
| 7,070,759 B2 * | 7/2006 | Fritzberg et al. ............ 424/1.65 |
| 7,094,885 B2 | 8/2006 | Fritzberg |
| 7,097,823 B2 * | 8/2006 | Fritzberg et al. ............ 424/1.65 |
| 7,115,720 B2 | 10/2006 | Fritzberg |
| 2002/0176818 A1 | 11/2002 | Fritzberg et al. |
| 2003/0118508 A1 | 6/2003 | Simon et al. |
| 2003/0158393 A1 | 8/2003 | Kasina |
| 2004/0096393 A1 | 5/2004 | Fritzberg |
| 2004/0126317 A1 | 7/2004 | Fritzberg |
| 2005/0063905 A1 | 3/2005 | Fritzberg et al. |
| 2005/0129667 A1 | 6/2005 | Fritzberg et al. |
| 2006/0140856 A1 | 6/2006 | Fritzberg |
| 2007/0053833 A1 | 3/2007 | Fritzberg et al. |

FOREIGN PATENT DOCUMENTS

| | | |
|---|---|---|
| EP | 0 164 843 | 12/1985 |
| EP | 0164843 | 12/1985 |
| EP | 0 210 043 | 1/1987 |
| EP | 0210043 | 1/1987 |
| EP | 0 232 751 | 8/1987 |
| EP | 0232751 | 8/1987 |
| EP | 0 255 471 | 2/1988 |
| EP | 0255471 | 2/1988 |
| EP | 0 258 616 | 3/1988 |
| EP | 0258616 | 3/1988 |
| EP | 0 287 465 | 10/1988 |
| EP | 0287465 | 10/1988 |
| EP | 0 374 501 | 6/1990 |
| EP | 0374501 | 6/1990 |
| EP | 0 382 582 | 8/1990 |
| EP | 0382582 | 8/1990 |
| EP | 0 408 701 | 1/1991 |
| EP | 0408701 | 1/1991 |
| EP | 0 411 941 | 2/1991 |
| EP | 0411941 | 2/1991 |
| EP | 0 455 380 | 11/1991 |
| EP | 0455380 | 11/1991 |
| EP | 0 698 029 | 2/1996 |
| EP | 0698029 | 2/1996 |
| EP | 0 972 528 | 1/2000 |
| EP | 0972528 | 1/2000 |
| FR | 2230374 | 12/1974 |
| WO | WO 84/03698 | 9/1984 |
| WO | WO-84/03698 | 9/1984 |
| WO | WO 90/06776 | 6/1990 |
| WO | WO-9006776 | 6/1990 |
| WO | WO-91/16075 | 10/1991 |
| WO | WO 91/16075 | 10/1991 |
| WO | WO 93/25240 | 12/1993 |
| WO | WO-93/25240 | 12/1993 |
| WO | WO-94/26753 | 11/1994 |
| WO | WO 94/26753 | 11/1994 |
| WO | WO 95/10940 | 4/1995 |
| WO | WO-95/10940 | 4/1995 |
| WO | WO 98/43678 | 10/1998 |
| WO | WO-98/43678 | 10/1998 |
| WO | WO 01/91806 | 12/2001 |
| WO | WO-0191806 | 12/2001 |
| WO | WO-02/062398 | 8/2002 |
| WO | WO 02/062398 | 8/2002 |

OTHER PUBLICATIONS

"Chapter III: Chemotherapy Regimens in Adults", *In Cancer Chemotherapy Pocket Guide*, Robert J. Ignoffo, Editor,(1998),248-255; 338-341.

"Manufacture of Triethylene Tetramine", *Research Disclosure*, 315, No. 31591,(1990),595.

"Multiple Myeloma", *In Clinical Oncology, A Multidisciplinary Approach for Physicians and Students*, 7th Edition, Philip Rubin, Editor,(1993),239-244.

"NeoRx Updates Skeletal Targeted Radiotherapy (STR) Phase I/II Trail Data", *NeoRx Press Release*, (May 7, 2001).

"NeoRx's Multiple Myeloma Study with Targeted Radiotherapy to be Updated at ASH—Recent Thalidomide Results Heighten Interest in New Multiple Myeloma Therapies", *NeoRx Press Release*, (Nov. 30, 1999).

"NeoRx's Targeted Radiotherapy Achieves Complete Responses with Excellent Safety in Multiple Myeloma Patients", *NeoRx Press Release*, (Dec. 7, 1999).

"Phase I/II Interim Data on NeoRx's STR Product in Multiple Myeloma", *NeoRx Press Release*, (1999).

Abrams, Paul , "High-Dose Targeted Radiation to Bone and Bone Metastases", *CaP Cure Meeting*, Lake Tahoe, NV, (2000),2 pages.

Alexanian, R , et al., "Impact of Complete Remission with Intensive Therapy in Patients with Responsive Multiple Myeloma", *British Journal of Hematology*, 27(10), (2001),1037-1043.

Anderson, et al., "High-Dose Samarium-153 Ethylene Diamine Tetramethylene Phosphonate: Low Toxicity of Skeletal Irradiation in Patients with Osteosarcoma and Bone Metastases", *Journal of Clinical Oncology*, 20, (2002),189-196.

Ando, A , et al., "177Lu-EDTMP: A Potential Therapeutic Bone Agent", *Nucl. Med. Commun*, 19(6), (1998),587-591.

Appelbaum, F R., et al., "Chronic and Acute Leukemias in Adults", *The Role of Marrow Transplantation in the Treatment of Leukemia*, Martinus Nijhoff Publisjers, Boston. C.D. Bloomfield, editor,(1985),229-262.

Appelbaum, F. R., et al., "Specific Marrow Ablation Before Marrow Transplantation Using an Aminophosphonic Acid Conjugate 166Ho-EDTMP", *Blood*, 80, (1992),1608-1613.

Bardies, M , et al., "Computational Methods in Radionuclide Dosimetry", *Physics in Medicine and Biology*, 41, (1996),1941-1955.

Barlogie, B , et al., "Prognostic Factors with High-Dose Melphalan for Refractory Multiple Myeloma.", *Blood*, 72(6), (Dec. 1988),2015-2019.

Bataille, R , et al., "Multiple Myeloma", *New England Journal of Medicine*, 336, (1997),1657-1664.

Bayouth, J. E., et al., "Dosimetry Considerations of Bone-Seeking Radionuclides for Marrow Ablation", *Medical Physics*, 20(4), (Jul.-Aug. 1993),1089-1096.

Bayouth, J. E., et al., "Pharmacokinetics, Dosimetry and Toxicity of Homium-166-DOTMP for Bone Marrow Ablation in Multiple Myeloma", *Journal of Nuclear Medicine*, 36(5), (May 1995),730-737.

Bayouth, J. E., et al., "Radiation Dose Distribution Within the Bone Marrow of Patients Receiving Holmium-166-Labeled-Phosphonate for Marrow Ablation", *Medical Physics*, 22(6), (Jun. 1995),743-753.

Bearman, et al., "Regimen-related Toxicity in Patients Undergoing Bone Marrow Transplantation", *Journal of Clinical Oncology*, 6(10), (Oct. 1988),1562-1568.

Beddoe, A H., et al., "Measurements of Trabecular Bone Structure in Man", *Physics in Medicine and Biology*, 21(4), (Jul. 1976),589-607.

Bensinger, et al., "166Ho-DOTMP and High-Dose Melphalan before Autologous Peripheral Blood Stem Cell Transplantation in Patients with Multiple Myeloma", Abstract P287; IXth International Workshop on Multiple Myeloma,(2003).

Bensinger, B , et al., "166Holmium-DOTMP Plus Standard High Dose Chemotherapy (HDC) with Autologous Transplant Produce High Rates of Complete Remission (CR) in Multiple Myeloma (MM) Patients: An Updated Report of a Phase I/II Study", *Proceedings of the American Society of Clinical Oncology*, 20, Abstract No. 18,(2001),5a.

Bensinger, W , et al., "Phase I/II Study of 166Holmium-DOTMP in Combination with Melphalan +/- Total Body Irradiation (TBI) with Autologous Peripheral Blood Stem Cell Transplant (PBSCT) for Patients with Multiple Myeloma", *Proceedings of the American Society of Clinical Oncology 2000*, 19, Abstract No. 26,(2000),9a.

Bensinger, et al., "Skeletal Targeted Radiotherapy (STR) with 166Ho-DOTMP plus Melphalan and Autologous Stem Cell Transplant (ASCT) in Multiple Myeloma(MM)", *Meeting Proceedings of ASCO*, 22, ASCO Annual Meeting, May 2003; Abstract No. 3346,(2003),833.

Bigler, R , et al., "Skeletal Distribution of Mineralized Bone Tissue in Humans", *Health Physics*, 31, (1976),213-218.

Boussiotis, V A., et al., "Bone Marrow Transplantation for Low-grade Lymphoma and Chronic Lymphocytic Leukemia", *Semin Hematol*, 36, (1999),209-216.

Breitz, H , "Dosimetry in a Myeloablative Setting", Annual Society of Nuclear Medicine Meeting, Continuing Education Course,(2001).

Breitz, H , et al., "Dosimetry in Myeloblative Setting", *Cancer Biother. Radiopharm.*, 17(1), (2002),119-128.

Breitz, et al., "Dosimetry of High Dose Skeletal targeted Radiotherapy (STR) with 166-Ho-DOTMP", *Cancer Biotherapy and Radiopharmaceuticals*, 18, (2003),225-230.

Breitz, H , et al., "Dosimetry of High Dose Skeletal Targeted Radiotherapy wit Ho-166 DOTMP", *Presentation at VIIth International Radiopharmaceutical Dosimetry Symposium*, (2002).

Breitz, H , et al., "Multiple Myeloma: Skeletal Targeted Radiotherapy with 166-Ho-DOTMP for Treatment of Multiple Myeloma", *Presented at "Targeted Radionuclide Therapy"*, (2002).

Breitz, H, "Quantitative Dosimetry Workup in a Myeloablative Setting", Presentation at the 48th Annual Society for Nuclear Medicine Meeting,(2001).

Champlin, R , et al., "166Holmium-DOTMP in Combination with Melphalan with or without Total Body Irradiation as a Preparative Regimen for Autologous Stem Cell Transplant (ASCT) for Patients with Multiple Myeloma (MM)", *Blood*, 94(10), American Society of Hematology, Abstract No. 3133,(1999),709a.

Champlin, R , et al., "Bone Marrow Transplantation for Acute Leukemia: Recent Advances and Comparison with Alternative Therapies", *Seminars in Hematology*, 24, (1987),55-67.

Champlin, R. , et al., "Holmium-166 DOTMP, A Bone Seeking Radiochelate for Selective Marrow Radiotherapy with Bone Marrow Transplantation (BMT) for Multiple Myeloma", *Experimental Hematology*, 21, Abstracts, 22nd Annual Meeting of the International Society for Experimental Hematology, Rotterdam, The Netherlands, Abstract No. 393,(1993),1117.

Champlin, R. , et al., "Holmium-166 DOTMP, A Bone Seeking Radiochelate For Selective Marrow Radiotherapy with Bone Marrow Transplantation (BMT) for Multiple Myeloma", *Blood*, 82, Abstracts, American Society of Hematology Thirty-Fifth Annual Meeting, St. Louis, MO, Abstract No. 1051,(1993),266a.

Champlin, R , et al., "Phase I/II Study of Targeted Radiotherapy Using 166Ho-DOTMP with Melphalan and Peripheral Blood Stem Cell Transplant for Multiple Myeloma", A slide presentation, International Society of Experimental Hematology,(2000).

Champlin, R , et al., "Role of Bone Marrow Transplantation in the Treatment of Hematologic Malignancies and Solid Tumors: Critical Review of Syngeneic, Autologous, and Allogeneic Transplants.", *Cancer Treatment Reports*, 68, (1984),145-161.

Champlin, R. , et al., "Two Phase I/II Studies of 166Holmium-DOTMP in Combination with Melphalan With or Without Total Body Irradiation as a Preparative Regimen for Autologous Stem Cell Transplant (PBSCT) for Patients with Multiple Myeloma", *Experimental Hematology*, 27(7), Abstract No. 196, Program and Abstracts, 28th Annual Meeting of the International Society for Experimental Hematology, Monte Carlo, Monaco.,(1999),88.

Cleynhens, et al., "99mTc-EC-AMDP, a Bone Agent with Rapid Clearance from Soft Tissue", *Technetium, Rhenium and Other Metals in Chemistry and Nuclear Medicine*, 5, (1999),605-609.

Cohen, et al., "Bisphosphonates and Tetracycline: Experimental Models for Their Evaluation in Calcium-Related Disorders", *Pharmaceutical Research*, 15, (1998),606-613.

Cunningham, D , et al., "High-dose Melphalan for Multiple Myeloma: Long-term Follow-up Data", *Journal of Clinical Oncology*, 12, (1994),764-768.

Dispenzieri, et al., "A Phase I Study of a Conditioning Regimen for Peripheral Stem Cell Transplantation (PBSCT) for Multiple Myeloma (MM): 153Samarium Ethylenediaminetetramethylenephosphonate (153SM-EDMPT) and Melphalan", *Blood*, 96, Abstract 2397,(2000),558a.

Dispenzieri, et al., "A Phase I/II Dose Escalation Study of 153-Samarium EDTMP (153-Sm-EDMTP) with Fixed Dose Melphalan Peripheral Stem Cell Transplantation (PBSCT) for Multiple Myeloma (MM)", *Blood*, 98, Abstract 2855,(2001),682a-683a.

Durrant, Simon , et al., "Sm-153 Lexidronam, Limb Irradiation and Stem Cell Transplantation for the Treatment of Multiple Myeloma", Amer. Soc. Hemeotology Annual Meeting, Orlando, FL.,(2001).

Eary, Janet F., et al., "Samarium-153-EDTMP Biodistribution and Dosimetry Estimation", *The Journal of Nuclear Medicine*, 34, (1993),1031-1036.

Eckerman, K, et al., "Dose Conversion Factors for Marrow and Bone by Skeletal Regions", *Journal of Nucler Medicine*, 35, (1994),112P.

Eisenhut, M, "Iodine-131-Labeled Diphosphonates for the Palliative Treatment of Bone Metastases: I. Organ Distribution and Kinetics of I-131 BDP3 in Rats", *The Journal of Nuclear Medicine*, 25, (1984),1356-1361.

Eisenhut, et al., "The Influence of Substituents in 99mTc-Benzylidenediphosphonate Complexes on their Organ Distribution in Rats", *Nuklearmedizin*, 23, (1984),119-122.

Firusian, N, et al., "Results of 89Strontium Therapy in Patients with Carcinoma of the Prostate and Incurable Pain from Bone Metastases: A Preliminary Report", *The Journal of Urology*116, (1976),764-768.

Fritzberg, Alan R., "Holmium-166 DOTMP for Marrow Ablation: Clinical Studies to Demonstrate Efficacy in Multiple Myeloma", Society of Nuclear Medicine Annual Meeting, St. Louis,(2000).

Fujisaki, et al., "Physicochemical Characterization of Bisphosphonic Carboxyfluorescein for Osteotropic Drug Delivery", *J Pharm Pharmacol.*, 48, (1996),798-800.

Garlich, J R., et al., "Chemical Considerations of 153Sm-EDTMP, a New Therapeutic Bone Agent", Sixth International Symposium on Radiopharmaceutical Chemistry: Abstracts. Boston, Jun. 29-Jul. 3, 1986. Paper 140,(1986),317-319.

Garlich, J. R., et al., "Chemistry of Novel Macrocyclic Aminophosphonic Acid Chelates of Rare Earth Radionuclides and Their in vivo Biodistribution", *The Journal of Nuclear Medicine*, 34, Abstract Book, Proceedings of the 40th Annual Meeting, Toronto, Ontario, Canada, Abstract No. 1134,(1993),244P.

Geraldes, C F., et al., "Synthesis, Protonation Sequence, and NMR Studies of Polyazamacrocyclic Methylenephosphonates", *Inorganic Chemistry*, 28, (1989),3336-3341.

Giralt, et al., "166Ho-DOTMP Plus Melphalan Followed by Peripheral Blood Stem Cell Transplantation in Patients with Multiple Myeloma: Results of Two Phase I/II Trials", *Blood*, Blood First Edition Paper; DOI 10.1182/2002-10-3250,(2003),1-38.

Giralt, S, et al., "Hemorrhagic Cystitis after Targeted Radiotherapy with Holmium-DOTMP (166HO) for Multiple Myeloma (MM) is Preventable with Bladder Irrigation", *Blood*, 96(11), Abstract No. 1686,(2000).

Giralt, et al., "Long-Term Follow-Up of 83 Patients with Multiple Myeloma (MM) Treated on a Phase I-II Study of Skeletal Targeted Radiotherapy (STR) Using 166Ho-DOTMP Plus Melphalan with or without Total Body Irradiation (TBI) and Autologous Hematopoietic Stem Cell . . . ", *Blood*, 100, 44th Annual Meeting of the American Society of Hematology; Abstract 670,(2002),179a.

Giralt, S, et al., "Preliminary Results of a Phase I/II Study of Multiple Myeloma (MM) Patients Treated with 166Holmium-DOTMP in Combination with High Dose Melphalan +/- Total Body Irradiation (TBI) with Autologous Stem Cell Transplant (ASCT)", *Blood*, 96(11), Abstract No. 2395,(2000).

Giralt, S, et al., "Results of a Phase I/II Trial with 166Ho-DOTMP Plus High Dose Chemotherapy in Patients with Multiple Myeloma", *VIIIth Int'l Multiple Myeloma Proceedings*, Abstract No. S24,(2001),40-41.

Giralt, S, et al., "Two Phase I/II Studies of 166Holmium-DOTMP in Combination with or without TBI as a Preparative Regimen for Autologous Stem Cell Transplant (PBSCT) for Patients with Multiple Myeloma", *VIIth Int'l Multiple Myeloma Workshop*, Abstract No. 033, Meeting Held Sep. 1-5, 1999,117.

Goeckeler, W F., et al., "Samarium-153 Radiotherapeutic Bone Agents", *Nucl. Med. Biol.*, 13, (1986),479-482.

Goldman, "Good Drug, Bad Luck: Business, Regulatory Issues Can Create Obstacles for Drug Development", *Journal of the National Cancer Institute*, 96, (2004),1573-1574.

Hassfjell, S. P., et al., "212Bi-DOTMP: An Alpha Particle Emitting Bone-Seeking Agent for Targeted Radiotherapy", *Nuclear Medicine and Biology*, 24, (1997),231-237.

Hogan, et al., "Successful Treatment of POEMS Syndrome with Autologous Hematopoietic Progenitor Cell Transplantation", *Bone Marrow Transplantation*, 28, (2001),305-309.

Hsia, C, et al., "Preparation of 113min-DTPMP Bone Scanning Agent and its Prliminary Clinical Application", *Chemical Abstracts*, 95, (1981),305.

Jarvis, et al., "Characterization of the Bisphosphonate Recognition Site on Hydroxyapatite Using Radioligand Binding Techniques with [14C]Citric Acid", *Calcif Tissue Int.*, 52, (1993),372-377.

John, E K., et al., "Formulation Development and Stability of the 166Ho-DOTMP for High Level Dosages—A Skeletal Targeted Radiotherapeutic", *Journal of Nuclear Medicine*, 42, Proceedings of the SNM 48th Annual Meeting, No. 1122,(2001),267P.

Kabachnik, I M., et al., "Synthesis and Acid-Base and Complex-Forming Properties of 1,4,7,10—Tetrakis (dihydroxyphosohorylmethyl)—1,4,7,10—tetraazacyclododecane", *Bulletin of the Academy of Sciences of the USSR; Division of Chemical Science*, 33, (1984),777-782.

Kabachnik, M I., et al., "Synthesis and Study of a New Complexone—N,N',N"—Tris-(Dihydroxyphosphorylmethyl)—1,4,7—Triazacyclononane", *Bulletin of the Academy of Sciences of the USSR; Division of Chemical Science*, 33, (1984),769-777.

Kaplan, E, et al., "Therapy of Carcinoma of the Prostate Metastic to Bone with P32 Labeled Condensed Phosphate", *The Journal of Nuclear Medicine*, 1, (1960),1-13.

Kasi, L. P., et al., "Ho-166DOTMP: A New Agent for Bone Marrow Ablation", *The Journal of Nuclear Medicine*, 34, Abstract Book, Proceedings of the 40th Annual Meeting, Toronto, Ontario, Canada, Abstract No. 125,(1993),33P.

Keeling, A. A., et al., "Yttrium-90-EDTMP: A Radiotherapeutic Agent in the Treatment of Leukaemias", *British Journal of Cancer*, 60, (1989), 74-78.

Ketring, A R., "153Sm-EDTMP and 186Re-HEDP as Bone Therapeutic Radiopharmaceuticals", *Nucl. Med. Biol.*, 14(3), (1987),223-232.

Kohn, D B., "The Current Status of Gene Therapy Using Hematopoietic Stem Cells", *Currunt Opinion in Pediatr.*, 7, (1995),56-63.

Kothari, K K., et al., "186RE and 188RE Phosphonate Ligands", *The Journal of Nuclear Medicine*, 40, Proceedings of the 46th Annual Meeting, Abstract No. 1015,(1999),228P.

Krishnamurthy, G. T., et al., "Tin-117m(4+)DTPA: Pharmacokinetics and Imaging Characteristics in Patients with Metastatic Bone Pain", *The Journal of Nuclear Medicine*, 38, (1997),230-237.

Krivit, W, et al., "Bone Marrow Transplantation as Effective Treatment of Central Nervous System Disease in Globoid Cell Leukodystrophy, metachromatic leukodystrophy, adrenoleukodystrophy, mannosidosis, fucosidosis, aspartylglucosaminuria, Hurler, Maroteaux-Lamy, and . . . ", *Curr Opin Neurol*, 12(2), (1999),167-176.

Kyle, et al., "Multiple Myeloma", *The New England Journal of Medicine*, 351, (2004),1860-1873.

Larsen, et al., "Preliminary Evaluation of a New Radiolabelled Bisphosphonate", *Journal of Labelled Compounds and Radiopharmaceuticals*, XLI, (1998),823-830.

Logan, K W., et al., "Radiation Dose Calculations in Persons Receiving Injection of Samarium-153-EDTMP", *J. Nucl. Med.*, 28, (1987),505-509.

Ma, J, et al., "Indium-113m Labeled Bone Imaging Agents—Animal Experiment and Clinical Application of 113mIn-DTPMP and 113mIn-EDTMP", *Chemical Abstracts*, 93, (1980),285.

Mathieu, L., et al., "Preparation of Rhenium-186 Labelled EHDP and its Possible Use in the Treatment of Osseous Neoplasms", *International Journal of Applied Radiation and Isotopes*, 30, (1979),725-727.

McCullough, S P., et al., "99mTc-MDP as a Surrogate Quantitative Imaging Agent for High Dose 166Ho-DOTMP Bone Marrow Ablation Therapy", *Society of Nuclear Medicine Proceedings of the 47th Annual Meeting*, 41(5), (2000),147P.

McCullough, S. P., et al., "Non-target Organ Doses in Patients Undergoing Bone Marrow Ablation with Ho-166-DOTMP", *The*

*Journal of Nuclear Medicine*, 39, No. 5, Abstract Book, Scientific Abstracts of the 45th Annual Meeting of the Society of Nuclear Medicine, Toronto, Ontario, Canada, Abstract No. 838,(1998),186P.

McCullough, S P., et al., "Pharmacokinetics and Patient Specific Dosimetry of High Dose 166Ho-DOTMP Therapy Used for Treatment of Breast Cancer Metastatic to Bone", *The Journal of Nuclear Medicine: Proceedings of the 46th Annual Meeting*, 40, (1999),40P.

McCullough, S P., et al., "Preliminary Correlation of Bone Marrow Dose Distributions and Disease Response in Multiple Myeloma Patients Treated with Target Sketetal Radiotherapy", *The Journal of Nuclear Medicine, Proceedings of the 47th Annual Meeting*, 41(5), Abstract No. 327,(2000),83P.

Moreau, P , et al., "Melphalan 220 mg/m2 Followed by Peripheral Blood Stem Cell Transplantation in 27 Patients with Advanced Multiple Myeloma", *Bone Marrow Transplant*, 23(10), (1999),1003-1006.

Nail, S L., "The Relationship Between the Structure of Aluminum Hydride Gel and Acid Reactivity", *Chemical Abstracts*, 84, (1976),353.

O'Mara, R E., et al., "Rare Earth Nuclides as Potential Agents for Skeletal Imaging", *The Journal of Nuclear Medicine*, 10, (1969),49-51.

Parks, N. J., et al., "Bone Marrow Transplantation in Dogs After Radio-Ablation with a New Ho-166 Amino Phosphonic Acid Bone-Seeking Agent (DOTMP)", *Blood*, 82 (1), (1993),318-325.

Paulson, Tom , "Seattle Leads in Stem Cell Study: Fred Hutchinson Team Explores Options with Autoimmune Project", *The Seattle Post-Intelligencer*, (1999).

Podoloff, D A., et al., "Phase I/II Studies of Holmium-166 DOTMP in Combination with Melphalan with or without Total Body Irradiation as a Preparative Regimen For Autologous Stem Cell Transplant (PBSCT) for Patients with Multiple Myeloma (MM)", *European Journal of Nuclear Medicine*, 26(9), Abstract No. PS-641,(1999),1213.

Podoloff, D. A., et al., "Phase I/II Study of Holmium-166-DOTMP for Bone Marrow Ablation in Multple Myeloma Prior to Bone Marrow Transplantation (BMT)", *The Journal of Nuclear Medicine*, 35. Abstract Book, Proceedings of the 41st Annual Meeting, Orlando, FL, Abstract No. 139,(1994),37P.

Podoloff, Donald A., "The Role of Radioisotopes and the Treatment of Solid Tumors", *Accomplishments with Medical Isotopes: Advanced Health Care for the 21st Century*, Medical Isotopes and the 21st Century,(1999).

Podoloff, D. A., et al., "Update on the Ho-166 DOTMP Bone Marrow Ablation Trial at U.T.M.D. Anderson Cancer Center", *Journal of Nuclear Medicine*, 37, Supplement: Radiolabeled IUdr, Abstract No. 1053,(1996),234P.

Rajendran, J G., et al., "High Dose Holmium-166 DOTMP Myeloablative Treatment for Multiple Myeloma", *Journal of Nuclear Medicine*, Proceedings of the 47th Annual Meeting,(2000),146P.

Rajendran, et al., "High-Dose 166Ho-DOTMP in Myeloablative Treatment of Multiple Myeloma: Pharmacokinetics, Biodistribution, and Absorbed Dose Estimation", *J Nucl Med*, 43, (2002),1383-1390.

Rajendran, J G., et al., "Holmium-166 DOTMP: An Agent with Ideal Physical and Pharmacokinetic Characteristics for Use in Myeloablative Treatment of Multiple Myeloma", *Western Regional Soc. Nucl. Med.*, (2000).

Rosch, F. , et al., "Radiation Doses of Yttrium-90 Citrate and Yttrium-90 EDTMP as Determined via Analogous Yttrium-86 Complexes and Positron Emission Tomography", *European Journal of Nuclear Medicine*, 23, (1996),958-966.

Rosoff, B , et al., "Distribution and Excretion of Radioactive Rare-Earth Compounds in Mice", *International Journal of Applied Radiation and Isotopes*, 14, (1962),129-135.

Saltus, Richard , "Double Transplant's Success May Lead to End of Rejection Drugs", *The Seattle Post-Intelligencer*, (1999).

Schmidt, C G., et al., "89-Sr for the Treatment of Incurable Pain in Patient with Neoplastic Osseous Infiltrations", *Int. J. Clin. Pharmacol*, 9, (1974),199-205.

Sherry, A D., "31P and 23Na NMR Lanthanide Induced Shifts in Axially Symmetric Macrocyclic Phosphonate Complexes ", *Inorganica Chimica Acta*, 139, (1987),137-139.

Sherry, A D., et al., "Dy(DOTP)5-: A New, Stable, 23Na Shift Reagent", *Journal of Magnetic Resonance*, 76, (1988),528-533.

Shibata, Y , et al., "Selectively Eliminated Blood Monocytes and Splenic Suppressor Macrophages in Mice Depleted of Bone Marrow by Strontium 89", *J. Leukocyte Biol.*, 38, (1985),659-669.

Simon, J , et al., "153Sm-EDTMP, a Potential Therapeutic Bone Agent", .Sixth International Symposium on Radiopharmaceutical Chemistry: Abstracts. Boston, Jun. 29-Jul. 3, 1986. Paper 141,(1986),320-322.

Spiers, F W., et al., "Mean Skeletal Dose Factors for Beta-particle Emitters in Human Bone. Part II: Surface-seeking Radionuclides", *British Journal of Radiology*, 54, (1981),500-504.

Srivastava, S C., et al., "Ruthenium-97 Labeled Compounds—A New Class of Radiopharmaceuticals", *Front. Nucl. Med.*, (*Sel. Pap. Int. Congr. World Fed. Nucl. Med. Biol.*), 2nd, Editor: Horst, Wolfgang (Ed), Wagner, Henry N., Jr. (Ed), Buchanan, Julia W (Ed),(1980),123-133.

Stabin, M G., et al., "Bremsstrahlung Radiation Dose in Yttrium-90 Therapy Applications", *J Nucl Med*, 35, (1994),1377-1380.

Subramanian, G , et al., "Indium-113m Labeled Polyfunctional Phosphonates as Bone Imaging Agents", *Chemical Abstracts*, 87, (1977),243.

Subramanian, G , et al., "Indium-113m-Labeled Polyfunctional Phosphonates as Bone-Imaging Agents", *Journal of Nuclear Medicine*, 16, (1975),1080-1084.

Subramanian, G , et al., "Localization of new Tc-99m Labeled Diphosphonates in Experimental Bone Lesions", Presented at the 19th International Annual Meeting of the Society of Nuclear Medicine Europe, Bern, Switzerland, Sep. 8-11, 1981.

Swailem, Fayez , et al., "In vivo Tissue Uptake and Retention of Sn-117m(4+)DTPA in a Human Subject with Metastatic Bone Pain and in Normal Mice", *Nuclear Medicine & Biology*, 25, (1988),279-287.

Tananaev, I V., et al., "Lanthanide Ethylenediametetramethylphosphonates", *Chemical Abstracts*, 96, (1982),553.

Thomas, E D., "Clinical Trials with Bone Marrow Transplantation", *Clinical Trials in Cancer Medicine*, Academic Press, Inc. ,(1985),239-253.

Thomas, E D., "Marrow Transplantation for Malignant Diseases", *Journal of Clinical Oncology*, 1, (1983),517-531.

Thomas, E D., et al., "Marrow Transplantation for Thalassemia", *Annals New York Academy of Sciences*, 445, (1985),417-427.

Thomas, S R., "MIRD Pamphlet No. 14: A Dynamic Urinary Bladder Model for Radiation Dose Calculations.", *Journal of Nuclear Medicine*, 33, Published erratum appears in Journal of Nuclear Medicine, 35, 73 (1994).,(1992),783-802.

Turner, J H., et al., "Radiopharmaceutical Therapy of 5T33 Murine Myeloma by Sequential Treatment with Samarium-153 Ethylenediaminetetramethylene Phosphonate, Melphalan, and Bone Marrow Transplantation", *Journal of the National Cancer Institute*, 85(18), (1993),1508-1513.

Turner, J. H., et al., "Samarium—153 EDTMP Therapy of Disseminated Skeletal Metastasis", *Eur J. Nucl Med*, 15, (1989),784-795.

Turner, J. H., et al., "Samarium-153 EDTMP and melphalan chemoradiotherapy regimen for bone marrow ablation prior to marrow transplantation in the C5t7BL/KalwRij mouse as a model for treatment of multiple myeloma", *Australian & New Zealand J of Medicine*, 22, (1992),405.

Turner, J. H., et al., "Samarium-153 EDTMP and melphalan chemoradiotherapy regimen for bonemarrow ablation prior to marrow transplantation: an experimental model in the rat", *Nuclear Medicine Communications*, 13(5), (1992),321-329.

Volkert, W A., et al., "Characteristcs of Tc-99m-Complexes of Large Tetraphosphonates", 1984 Abstract Form for Scientific Exhibits Society of Nuclear Medicine 31st Annual Meeting, Los Angeles, California, Jun. 5-8, 1984.

Weininger, J , "Re-186 HEDP: A Potential Therapeutic Bone Agent", *Journal of Nuclear Medicine*, 24(5), Proceedings of the 30th Annual Meeting—Posters,(1983),p. 125.

Wendt, R E., "An Improved Estimate of Activity in Skull-Like Structures", *Journal of Nuclear Medicine*, 42, Proceedings of the 48th Annual Meeting,(2001),193P.

Wendt, R E., et al., "Correction of Scatter and Septal Penetration in Ho-166 Images to Enable Narrow Beam Attenuation Correction", *Journal of Nuclear medicine*, 43(5),(2002),221P-222P.

Winston, M A., "Radioisotope Therapy in Bone and Joint Disease", *Seminars in Nuclear Medicine*, 9, (1979),114-120.

Wiseman, et al., "Bone Targeted Radioisotope Therapy for Treatment of Multiple Myeloma and Bone Tumors", *International Journal of Cancer Supplement*, 13, Abstract O 109; 18th UICC International Cancer Congress Oslo, Norway, Jun. 30-Jul. 5, 2002,104.

Wiseman, et al., "Residual Whole Body 153Samarium Activity Predicts for Successful Autologous Peripheral Blood Progenitor Cell (PBPC) Engraftment Following High Dose 153Samarium Ethylene Diamine Tetramethylene Phosphonate (153Sm-EDTMP) Targeted Radiotherapy", *Blood*, 96, Abstract 1811,(2000),421.

Young, J C., et al., "High Dose Samarium-153 Ethylenediaminetetramethylene Phosphate (SM-153 EDTMP) in the Treatment of Bone Sarcomas", *The Journal of Nuclear Medicine*, 40(5), Proceedings of the 46th Annual Meeting,(1999),219P.

Zeevaart, Jan R., et al., "Metal-ion Speciation in Blood Plasma Incorporating the Bisphosphonate, 1-hydroxy-4-aminopropilydenediphosphonate (APD), in Therapeutic Radiopharmaceuticals", *Journal of Inorganic Biochemistry*, 73, (1999),265-272.

"Communication pursuant to Article 96(2) EPC for corresponding European Patent Application No. 00944644.4", (May 2, 2007) ,6 pgs.

Blumenthal, R. D., et al., "Use of Antioxidant Vitamins to Reduce Radioimmunotherapy-Induced Gastrointestinal and Hematopoietic Toxicity", *Proceedings of the 90th Annual Meeting of the American Association for Cancer Research*, vol. 40, (Abstract #4227), (Mar. 1999), p. 641.

Tofe, A. J., et al., "Antioxidant Stabilization of Bone Agents", *Radiopharmaceuticals II: Proceedings of the 2nd International Symposium on Radiopharmaceuticals*, (Mar. 19-22, 1979, Seattle, Washington), (1979), 637-644.

Tofe, A. J., et al., "Antioxidant Stabilization of Bone Agents", *American Journal of Roentgenology*, 132(3), (Abstract No. 42, International Symposium on Radiopharmaceuticals), (Mar. 1979), p. 493.

Tofe, A. J., et al., "In Vitro Stabilization of a Low-Tin Bone-Imaging Agent ($^{99m}$Tc-Sn-HEDP) by Ascorbic Acid", *Journal of Nuclear Medicine*, 17(9), (1976), 820-825.

"U.S. Appl. No. 11/359,744 Non-Final Office Action mailed Jul. 10, 2007".

"Bone Cancer Therapy Project Funding Awarded to Brookhaven National Laboratory for Diatide-Licensed Product", Distribution: Business Editors and Health/Medical Writers (1999).

"Breast Cancer; Genitourinary Cancer; Multiple Myeloma", *Annotated Guide to Cancer Chemotherapeutic Regimens 1999/2000*, Oncology Special Edition,13-14; 17-18; 32.

"Chapter III: Chemotherapy Regimens in Adults", *In Cancer Chemotherapy Pocket Guide*, Robert J. Ignoffo, Editor, 248-255; 338-341 (1998).

"Multiple Myeloma", *In Clinical Oncology, A Multidisciplinary Approach for Physicians and Students, 7th Edition*, Philip Rubin, Editor, 239-244 (1993).

"NeoRx Updates Skeletal Targeted Radiotherapy (STR) Phase I/II Trail Data", *NeoRx Press Release* (2001).

"NeoRx's Multiple Myeloma Study with Targeted Radiotherapy to be Updated at ASH—Recent Thalidomide Results Heighten Interest in New Multiple Myeloma Therapies", *NeoRx Press Release* (1999).

"NeoRx's Targeted Radiotherapy Achieves Complete Responses with Excellent Safety in Multiple Myeloma Patients", *NeoRx Press Release* (1999).

"Phase I/II Interim Data on NeoRx's STR Product in Multiple Myeloma", *NeoRx Press Release* (1999).

Abrams, "High-Dose Targeted Radiation to Bone and Bone Metastases", *CaP Cure Meeting*, Lake Tahoe, NV, 2 pages (2000).

Alexanian et al., "Impact of Complete Remission with Intensive Therapy in Patients with Responsive Multiple Myeloma", *British Journal of Hematology*, 27(10), 1037-1043 (2001).

Anderson et al., "High-Dose Samarium-153 Ethylene Diamine Tetramethylene Phosphonate: Low Toxicity of Skeletal Irradiation In Patients with Osteosarcoma and Bone Metastases", *Journal of Clinical Oncology*, 20, 189-196 (2002).

Ando et al., "177Lu-EDTMP: A Potential Therapeutic Bone Agent", *Nucl. Med. Commun*, 19(6), 587-591 (1998).

Appelbaum et al., "Chronic and Acute Leukemias in Adults", *The Role of Marrow Transplantation in the Treatment of Leukemia*, Martinus Nijhoff Publisjers, Boston. C.D. Bloomfield, editor, 229-262 (1985).

Appelbaum et al., "Specific Marrow Ablation Before Marrow Transplantation Using an Aminophosphonic Acid Conjugate 166Ho-EDTMP", *Blood*, 80, 1608-1613 (1992).

Bardies et al., "Computational Methods in Radionuclide Dosimetry", *Physics in Medicine and Biology*, 41, 1941-1955 (1996).

Barlogie et al., "Prognostic Factors with High-Dose Melphalan for Refractory Multiple Myeloma.", *Blood*, 72(6), 2015-2019 (1988).

Bataille et al., "Multiple Myeloma", *New England Journal of Medicine*, 336, 1657-1664 (1997).

Bayouth et al., "Dosimetry Considerations of Bone-Seeking Radionuclides for Marrow Ablation", *Medical Physics*, 20(4), 1089-1096 (1993).

Bayouth et al., "Pharmacokinetics, Dosimetry and Toxicity of Homium-166-DOTMP for Bone Marrow Ablation in Multiple Myeloma", *Journal of Nuclear Medicine*, 36(5), 730-737 (1995).

Bayouth et al., "Radiation Dose Distribution Within the Bone Marrow of Patients Receiving Holmium-166-Labeled-Phosphonate for Marrow Ablation", *Medical Physics*, 22(6), 743-753 (1995).

Bearman et al., "Regimen-related Toxicity in Patients Undergoing Bone Marrow Transplantation", *Journal of Clinical Oncology*, 6(10), 1562-1568 (1988).

Beddoe et al., "Measurements of Trabecular Bone Structure in Man", *Physics in Medicine and Biology*, 21(4), 589-607 (1976).

Bensinger et al., "166Ho-DOTMP and High-Dose Melphalan before Autologous Peripheral Blood Stem Cell Transplantation in Patients with Multiple Myeloma", Abstract P287; IXth International Workshop on Multiple Myeloma (2003).

Bensinger, B , et al., "166Holmium-DOTMP Plus Standard High Dose Chemotherapy (HDC) with Autologous Transplant Produce High Rates of Complete Remission (CR) in Multiple Myeloma (MM) Patients: An Updated Report of a Phase I/II Study", *Proceedings of the American Society of Clinical Oncology*, 20, Abstract No. 18, 5a (2001).

Bensinger et al., "Phase I/II Study of 166Holmium-DOTMP in Combination with Melphalan +/− Total Body Irradiation (TBI) with Autologous Peripheral Blood Stem Cell Transplant (PBSCT) for Patients with Multiple Myeloma", *Proceedings of the American Society of Clinical Oncology 2000*, 19, Abstract No. 26, 9a (2000).

Bensinger et al., "Skeletal Targeted Radiotherapy (STR) with 166Ho-DOTMP plus Melphalan and Autologous Stem Cell Transplant (ASCT) in Multiple Myeloma(MM)", *Meeting Proceedings of ASCO*, 22, ASCO Annual Meeting, May 2003; Abstract No. 3346, 833 (2003).

Bigler et al., "Skeletal Distribution of Mineralized Bone Tissue in Humans", *Health Physics*, 31, 213-218 (1976).

Boussiotis et al., "Bone Marrow Transplantation for Low-grade Lymphoma and Chronic Lymphocytic Leukemia", *Semin Hematol*, 36, 209-216 (1999).

Breitz, "Dosimetry in a Myeloablative Setting", Annual Society of Nuclear Medicine Meeting, Continuing Education Course (2001).

Breitz et al., "Dosimetry in Myeloblative Setting", *Cancer Biother. Radiopharm.*, 17(1), 119-128 (2002).

Breitz et al., "Dosimetry of High Dose Skeletal Targeted Radiotherapy (STR) with 166-Ho-DOTMP", *Cancer Biotherapy and Radiopharmaceuticals*, 18, 225-230 (2003).

Breitz et al., "Dosimetry of High Dose Skeletal Targeted Radiotherapy wit Ho-166 DOTMP", *Presentation at VIIth International Radiopharmaceutical Dosimetry Symposium* (2002).

Breitz et al., "Multiple Myeloma: Skeletal Targeted Radiotherapy with 166-Ho-DOTMP for Treatment of Multiple Myeloma", *Presented at "Targeted Radionuclide Therapy"* (2002).

Breitz, "Quantitative Dosimetry Workup in a Myeloablative Setting", Presentation at the 48th Annual Society for Nuclear Medicine Meeting (2001).

Champlin et al., "166Holmium-DOTMP in Combination with Melphalan with or without Total Body Irradiation as a Preparative Regimen for Autologous Stem Cell Transplant (ASCT) for Patients with Multiple Myeloma (MM)", *Blood*, 94(10), American Society of Hematology, Abstract No. 3133, 709a (1999).

Champlin et al., "Bone Marrow Transplantation for Acute Leukemia: Recent Advances and Comparison with Alternative Therapies", *Seminars in Hematology*, 24, (1987),55-67.

Champlin et al., "Holmium-166 DOTMP, A Bone Seeking Radiochelate for Selective Marrow Radiotherapy with Bone Marrow Transplantation (BMT) for Multiple Myeloma", *Experimental Hematology*, 21, Abstracts, 22nd Annual Meeting of the International Society for Experimental Hematology, Rotterdam, The Netherlands, Abstract No. 393, 1117 (1993).

Champlin et al., "Holmium-166 DOTMP, A Bone Seeking Radiochelate For Selective Marrow Radiotherapy with Bone Marrow Transplantation (BMT) for Multiple Myeloma", *Blood*, 82, Abstracts, American Society of Hematology Thirty-Fifth Annual Meeting, St. Louis, MO, Abstract No. 1051, 266a (1993).

Champlin et al., "Phase I/II Study of Targeted Radiotherapy Using 166Ho-DOTMP with Melphalan and Peripheral Blood Stem Cell Transplant for Multiple Myeloma", A slide presentation, International Society of Experimental Hematology (2000).

Champlin et al., "Role of Bone Marrow Transplantation in the Treatment of Hematologic Malignancies and Solid Tumors: Critical Review of Syngeneic, Autologous, and Allogeneic Transplants.", *Cancer Treatment Reports*, 68, 145-161 (1984).

Champlin et al., "Two Phase I/II Studies of 166Holmium-DOTMP in Combination with Melphalan With or Without Total Body Irradiation as a Preparative Regimen for Autologous Stem Cell Transplant (PBSCT) for Patients with Multiple Myeloma", *Experimental Hematology*, 27(7), Abstract No. 196, Program and Abstracts, 28th Annual Meeting of the International Society for Experimental Hematology, Monte Carlo, Monaco., 88 (1999).

Cleynhens et al., "9mTc-EC-AMDP, a Bone Agent with Rapid Clearance from Soft Tissue", *Technetium, Rhenium and Other Metals in Chemistry and Nuclear Medicine*, 5, 605-609 (1999).

Cohen et al., "Bisphosphonates and Tetracycline: Experimental Models for Their Evaluation in Calcium-Related Disorders", *Pharmaceutical Research*, 15, 606-613 (1998).

Cunningham et al., "High-dose Melphalan for Multiple Myeloma: Long-Term Follow-up Data", *Journal of Clinical Oncology*, 12, 764-768 (1994).

Dispenzieri et al., "A Phase I Study of a Conditioning Regimen for Peripheral Stem Cell Transplantation (PBSCT) for Multiple Myeloma (MM): 153Samarium Ethylenediaminetetramethylenephosphonate (153SM-EDMPT) and Melphalan", *Blood*, 96, Abstract 2397, 558a (2000).

Dispenzieri et al., "A Phase I/II Dose Escalation Study of 153-Samarium EDTMP (153-Sm-EDMTP) with Fixed Dose Melphalan Peripheral Stem Cell Transplantation (PBSCT) for Multiple Myeloma (MM)", *Blood*, 98, Abstract 2855, 682a-683a (2001).

Durrant et al., "Sm-153 Lexidronam, Limb Irradiation and Stem Cell Transplantation for the Treatment of Multiple Myeloma", Amer. Soc. Hemeotology Annual Meeting, Orlando, FL. (2001).

Eary et al., "Samarium-153-EDTMP Biodistribution and Dosimetry Estimation", *The Journal of Nuclear Medicine*,34, 1031-1036 (1993).

Eckerman et al., "Dose Conversion Factors for Marrow and Bone by Skeletal Regions", *Journal of Nucler Medicine*, 35, 112P (1994).

Eisenhut, "Iodine-131-Labeled Diphosphonates for the Palliative Treatment of Bone Metastases: I. Organ Distribution and Kinetics of I-131 BDP3 in Rats", *The Journal of Nuclear Medicine*, 25, 1356-1361 (1984).

Eisenhut et al., "The Influence of Substituents in 99mTc-Benzylidenediphosphonate Complexes on their Organ Distribution in Rats", *Nuklearmedizin*,23, (1984), 119-122.

Firusian et al., "Results of 89Strontium Therapy in Patients with Carcinoma of the Prostate and Incurable Pain from Bone Metastases: A Preliminary Report", *The Journal of Urology*, 116, 764-768 (1976).

Fritzberg, "Holmium-166 DOTMP for Marrow Ablation: Clinical Studies to Demonstrate Efficacy in Multiple Myeloma", Society of Nuclear Medicine Annual Meeting, St. Louis (2000), abstract.

Fujisaki et al., "Physicochemical Characterization of Bisphosphonic Carboxyfluorescein for Osteotropic Drug Delivery", *J Pharm Pharmacol.*, 48, 798-800 (1996).

Garlich et al., "Chemical Considerations of 153Sm-EDTMP, a New Therapeutic Bone Agent", Sixth International Symposium on Radiopharmaceutical Chemistry: Abstract. Boston, Jun. 29-Jul. 3, 1986. Paper 140, 317-319 (1986).

Garlich et al., "Chemistry of Novel Macrocyclic Aminophosphonic Acid Chelates of Rare Earth Radionuclides and Their in vivo Blodistribution", *The Journal of Nuclear Medicine*, 34, Abstract Book, Proceedings of the 40th Annual Meeting, Toronto, Ontario, Canada, Abstract No. 1134, 244P (1993).

Geraldes et al., "Synthesis, Protonation Sequence, and NMR Studies of Polyazamacrocyclic Methylenephosphonates", *Inorganic Chemistry*, 28, 3336-3341 (1989).

Giralt et al., "166Ho-DOTMP Plus Melphalan Followed by Peripheral Blood Stem Cell Transplantation in Patients with Multiple Myeloma: Results of Two Phase I/II Trials", *Blood*, Blood First Edition Paper; DOI 10.1182/2002-10-3250, 1-38 (2003).

Giralt et al., "Hemorrhagic Cystitis after Targeted Radiotherapy with Holmium-DOTMP (166HO) for Multiple Myeloma (MM) is Preventable with Bladder Irrigation", *Blood*, 96(11), Abstract No. 1686 (2000).

Giralt et al., "Long-Term Follow-Up of 83 Patients with Multiple Myeloma (MM) Treated on a Phase I-II Study of Skeletal Targeted Radiotherapy (STR) Using 166Ho-DOTMP Plus Melphalan with or without Total Body Irradiation (TBI) and Autologous Hematopoietic Stem Cell . . . ", *Blood*, 100, 44th Annual Meeting of the American Society of Hematology; Abstract 670, 179a (2002).

Giralt et al., "Preliminary Results of a Phase I/II Study of Multiple Myeloma (MM) Patients Treated with 166Holmium-DOTMP in Combination with High Dose Melphalan +/− Total Body Irradiation (TBI) with Autologous Stem Cell Transplant (ASCT)", *Blood*, 96(11), Abstract No. 2395 (2000).

Giralt et al., "Results of a Phase I/II Trial with 166Ho-DOTMP Plus High Dose Chemotherapy in Patients with Multiple Myeloma", *VIIIth Int'l Multiple Myeloma Proceedings*, Abstract No. S24, 40-41 (2001).

Giralt et al., "Two Phase I/II Studies of 166Holmium-DOTMP in Combination with or without TBI as a Preparative Regimen for Autologous Stem Cell Transplant (PBSCT) for Patients with Multiple Myeloma", *VIIth Int'l Multiple Myeloma Workshop*, Abstract No. 033, 117 (1999).

Goeckeler et al., "Samarium-153 Radiotherapeutic Bone Agents", *Nucl. Med. Biol.*, 13, 479-482 (1986).

Hassfjell et al., "212Bi-DOTMP: An Alpha Particle Emitting Bone-Seeking Agent for Targeted Radiotherapy", *Nuclear Medicine and Biology*, 24, 231-237 (1997).

Hogan et al., "Successful Treatment of POEMS Syndrome with Autologous Hematopoietic Progenitor Cell Transplantation", *Bone Marrow Transplantation*, 28, 305-309 (2001).

Hsia et al., "Preparation of 113min-DTPMP Bone Scanning Agent and its Prliminary Clinical Application", *Chemical Abstracts*, 95, 305 (1981).

Jarvis et al., "Characterization of the Bisphosphonate Recognition Site on Hydroxyapatite Using Radioligand Binding Techniques with [14C]Citric Acid", *Calcif Tissue Int.*, 52, 372-377 (1993).

John et al., "Formulation Development and Stability of the 166Ho-DOTMP for High Level Dosages—A Skeletal Targeted Radiotherapeutic", *Journal of Nuclear Medicine*, 42, Proceedings of the SNM 48th Annual Meeting, No. 1122, 267P (2001).

Kabachnik et al., "Synthesis and Acid-Base and Complex-Forming Properties of 1,4,7,10—Tetrakis (dihydroxyphosohorylmethyl)—1,4,7,10—tetraazacyclododecane", *Bulletin of the Academy of Sciences of the USSR; Division of Chemical Science*, 33, 777-782, (1984).

Kabachnik et al., "Synthesis and Study of a New Complexone—N,N',N"—Tris-(Dihydroxyphosphorylmethyl)—1,4,7—Triazacyclononane", *Bulletin of the Academy of Sciences of the USSR; Division of Chemical Science*, 33, 769-777 (1984).

Kaplan et al., "Therapy of Carcinoma of the Prostate Metastic to Bone with P32 Labeled Condensed Phosphate", *The Journal of Nuclear Medicine*, 1, 1-13 (1960).

Kasi et al., "Ho-166DOTMP: A New Agent for Bone Marrow Ablation", *The Journal of Nuclear Medicine*, 34, Abstract Book, Proceedings of the 40th Annual Meeting, Toronto, Ontario, Canada, Abstract No. 125, 33P (1993).

Keeling et al., "Yttrium-90-EDTMP: A Radiotherapeutic Agent in the Treatment of Leukaemias", *British Journal of Cancer*, 60, 74-78 (1989).

Ketring, "153Sm-EDTMP and 186Re-HEDP as Bone Therapeutic Radiopharmaceuticals", *Nucl. Med. Biol.*, 14(3), 223-232 (1987).

Kohn, "The Current Status of Gene Therapy Using Hematopoietic Stem Cells", *Currunt Opinion in Pediatr.*, 7, 56-63 (1995).

Kothari et al., "186RE and 188RE Phosphonate Ligands", *The Journal of Nuclear Medicine*, 40, Proceedings of the 46th Annual Meeting, Abstract No. 1015, 228P (1999).

Krishnamurthy et al., "Tin-117m(4+)DTPA: Pharmacokinetics and Imaging Characteristics in Patients with Metastatic Bone Pain", *The Journal of Nuclear Medicine*, 38, 230-237 (1997).

Krivit et al., "Bone Marrow Transplantation as Effective Treatment of Central Nervous System Disease in Globold Cell Leukodystrophy, metachromatic leukodystrophy, adrenoleukodystrophy, mannosidosis, fucosidosis, aspartylglucosaminuria, Hurler, Maroteaux-Lamy, and ...", *Curr Opin Neurol*, 12(2), 167-176 (1999).

Larsen et al., "Preliminary Evaluation of a New Radiolabelled Bisphosphonate", *Journal of Labelled Compounds and Radiopharmaceuticals*, XLI, 823-830 (1998).

Logan et al., "Radiation Dose Calculations in Persons Receiving Injection of Samarium-153-EDTMP", *J. Nucl. Med.*, 28, 505-509 (1987).

Ma et al., "Indium-113m Labeled Bone Imaging Agents—Animal Experiment and Clinical Application of 113mIn-DTPMP and 113mIn-EDTMP", *Chemical Abstracts*, 93, 285 (1980).

Mathieu et al., "Preparation of Rhenium-186 Labelled EHDP and its Possible Use in the Treatment of Osseous Neoplasms", *International Journal of Applied Radiation and Isotopes*, 30, 725-727 (1979).

McCullough et al., "99mTc-MDP as a Surrogate Quantitative Imaging Agent for High Dose 166Ho-DOTMP Bone Marrow Ablation Therapy", *Society of Nuclear Medicine Proceedings of the 47th Annual Meeting*, 41(5), 147P (2000).

McCullough et al., "Non-target Organ Doses in Patients Undergoing Bone Marrow Ablation with Ho-166-DOTMP", *The Journal of Nuclear Medicine*, 39, No. 5, Abstract Book, Scientific Abstracts of the 45th Annual Meeting of the Society of Nuclear Medicine, Toronto, Ontario, Canada, Abstract No. 838, 186P (1998).

McCullough et al., "Pharmacokinetics and Patient Specific Dosimetry of High Dose 166Ho-DOTMP Therapy Used for Treatment of Breast Cancer Metastatic to Bone", *The Journal of Nuclear Medicine: Proceedings of the 46th Annual Meeting*, 40, 40P (1999).

McCullough et al., "Preliminary Correlation of Bone Marrow Dose Distributions and Disease Response in Multiple Myeloma Patients Treated with Target Sketetal Radiotherapy", *The Journal of Nuclear Medicine, Proceedings of the 47th Annual Meeting*, 41(5), Abstract No. 327, 83P (2000).

Moreau et al., "Melphalan 220 mg/m2 Followed by Peripheral Blood Stem Cell Transplantation in 27 Patients with Advanced Multiple Myeloma", *Bone Marrow Transplant*, 23(10), 1003-1006 (1999).

Nail, "The Relationship Between the Structure of Aluminum Hydride Gel and Acid Reactivity", *Chemical Abstracts*, 84, 353 (1976).

O'Mara et al., "Rare Earth Nuclides as Potential Agents for Skeletal Imaging", *The Journal of Nuclear Medicine*, 10, 49-51 (1969).

Parks et al., "Bone Marrow Transplantation in Dogs After Radio-Ablation with a New Ho-166 Amino Phosphonic Acid Bone-Seeking Agent (DOTMP)", *Blood*, 82(1), 318-325 (1993).

Paulson, "Seattle Leads in Stem Cell Study: Fred Hutchinson Team Explores Options with Autoimmune Project", *The Seattle Post-Intelligencer* (1999).

Podoloff et al., "Phase I/II Studies of Holmium-166 DOTMP in Combination with Melphalan with or without Total Body Irradiation as a Preparative Regimen For Autologous Stem Cell Transplant (PBSCT) for Patients with Multiple Myeloma (MM)", *European Journal of Nuclear Medicine*, 26(9), Abstract No. PS-641, 1213 (1999).

Podoloff et al., "Phase I/II Study of Holmium-166-DOTMP for Bone Marrow Ablation in Multple Myeloma Prior to Bone Marrow Transplantation (BMT)", *The Journal of Nuclear Medicine*, 35, Abstract Book, Proceedings of the 41st Annual Meeting, Orlando, FL, Abstract No. 139, 37P (1994).

Podoloff, "The Role of Radioisotopes and the Treatment of Solid Tumors", *Accomplishments with Medical Isotopes: Advanced Health Care for the 21st Century*, Medical Isotopes and the 21st Century (1999).

Podoloff et al., "Update on the Ho-166 DOTMP Bone Marrow Ablation Trial at U.T.M.D. Anderson Cancer Center", *Journal of Nuclear Medicine*, 37, Supplement: Radiolabeled IUdr, Abstract No. 1053, 234P (1996).

Rajendran et al., "High Dose Holmium-166 DOTMP Myeloabiative Treatment for Multiple Myeloma", *Journal of Nuclear Medicine, Proceedings of the 47th Annual Meeting*, 146P (2000).

Rajendran et al., "High-Dose 166Ho-DOTMP in Myeloablative Treatment of Multiple Myeloma: Pharmacokinetics, Blodistribution, and Absorbed Dose Estimation", *J Nucl Med*, 43, 1383-1390 (2002).

Rajendran et al., "Holmium-166 DOTMP: An Agent with Ideal Physical and Pharmacokinetic Characteristics for Use in Myeloablative Treatment of Multiple Myeloma", *Western Regional Soc. Nucl. Med.*, (2000).

Rosch et al., "Radiation Doses of Yttrium-90 Citrate and Yttrium-90 EDTMP as Determined via Analogous Yttrium-86 Complexes and Positron Emission Tomography", *European Journal of Nuclear Medicine*, 23, 958-966 (1996).

Rosoff et al., "Distribution and Excretion of Radioactive Rare-Earth Compounds in Mice", *International Journal of Applied Radiation and Isotopes*, 14, 129-135 (1962).

Saltus, "Double Transplant's Success May Lead to End of Rejection Drugs", *The Seattle Post-Intelligencer* (1999).

Schmidt et al., "89-Sr for the Treatment of Incurrable Pain in Patient with Neoplastic Osseous Infiltrations", *Int. J. Clin. Pharmacol*, 9, 199-205 (1974).

Sherry, "31P and 23Na NMR Lanthanide Induced Shifts in Axially Symmetric Macrocyclic Phosphonate Complexes", *Inorganica Chimica Acta*, 139, 137-139 (1987).

Sherry et al., "Dy(DOTP)5-: A New, Stable, 23Na Shift Reagent", *Journal of Magnetic Resonance*, 76, 528-533 (1988).

Shibata et al., "Selectively Eliminated Blood Monocytes and Splenic Suppressor Macrophages in Mice Depleted of Bone Marrow by Strontium 89", *J. Leukocyte Biol.*, 38, 659-669 (1985).

Simon et al., "153Sm-EDTMP, a Potential Therapeutic Bone Agent", Sixth International Symposium on Radiopharmaceutical Chemistry: Abstracts. Boston, Jun. 29-Jul. 3, 1986. Paper 141, 320-322 (1986).

Spiers et al., "Mean Skeletal Dose Factors for Beta-particle Emitters In Human Bone. Part II: Surface-seeking Radionuclides", *British Journal of Radiology*, 54, 500-504 (1981).

Srivastava et al., "10Ruthenium-97 Labeled Compounds—A New Class of Radiopharmaceuticals", *Medical Department, Brookhaven National Laboratory*, Upton, NY 11973, 123-133, date not available.

Stabin et al., "Bremsstrahlung Radiation Dose in Yttrium-90 Therapy Applications", *J Nucl Med*, 35, 1377-1380 (1994).

Subramanian et al., "Indium-113m Labeled Polyfunctional Phosphonates as Bone Imaging Agents", *Chemical Abstracts*, 87, 243 (1977).

Subramanian et al., "Indium-113m-Labeled Polyfunctional Phosphonates as Bone-Imaging Agents", *Journal of Nuclear Medicine*, 16, 1080-1084 (1975).

Subramanian et al., "Localization of new Tc-99m Labeled Diphosphonates in Experimental Bone Lesions", Presented at the 19th International Annual Meeting of the Society of Nuclear Medicine Europe, Bern, Switzerland, Sep. 8-11, 1981.

Swailem et al., "In vivo Tissue Uptake and Retention of Sn-117m(4+)DTPA in a Human Subject with Metastatic Bone Pain and in Normal Mice", *Nuclear Medicine & Biology*, 25, 279-287 (1988).

Tananaev et al., "Lanthanide Ethylenediametetramethylphosphonates", *Chemical Abstracts*, 96, 553 (1982).

Thomas, "Clinical Trials with Bone Marrow Transplantation", *Clinical Trials in Cancer Medicine*, Academic Press, Inc., 239-253 (1985).

Thomas, "Marrow Transplantation for Malignant Diseases", *Journal of Clinical Oncology*, 1, 517-531 (1983).

Thomas et al., "Marrow Transplantation for Thalassemia", *Annals New York Academy of Sciences*, 445, 417-427 (1985).

Thomas, "MIRD Pamphlet No. 14: A Dynamic Urinary Bladder Model for Radiation Dose Calculations.", *Journal of Nuclear Medicine*, 33, Published erratum appears in Journal of Nuclear Medicine, 35, 73 (1994), 783-802 (1992).

Turner et al., "Radiopharmaceutical Therapy of 5T33 Murine Myeloma by Sequential Treatment with Samarium-153 Ethylenediaminetetramethylene Phosphonate, Melphalan, and Bone Marrow Transplantation", *Journal of the National Cancer Institute*, 85(18), 1508-1513 (1993).

Turner et al., "Samarium—153 EDTMP Therapy of Disseminated Skeletal Metastasis", *Eur J. Nucl Med*, 15, 784-795 (1989).

Turner et al., "Samarium-153 EDTMP and melphalan chemoradiotherapy regimen for bone marrow ablation prior to marrow transplantation in the C5t7BL/KalwRij mouse as a model for treatment of multiple myeloma", *Australian & New Zealand J of Medicine*, 22, 405 (1992).

Turner et al., "Samarium-153 EDTMP and melphalan chemoradiotherapy regimen for bonemarrow ablation prior to marrow transplantation: an experimental model in the rat", *Nuclear Medicine Communications*, 13(5), 321-329 (1992).

Volkert et al., "Characteristcs of Tc-99m-Complexes of Large Tetraphosphonates", 1984 Abstract Form for Scientific Exhibits Society of Nuclear Medicine 31st Annual Meeting, Los Angeles, California, Jun. 5-8, 1984.

Weininger, "Re-186 HEDP: A Potential Therapeutic Bone Agent", 24(5), Proceedings of the 30th Annual Meeting—Posters, p. 125, 1983.

Wendt, "An Improved Estimate of Activity in Skull-Like Structures", *Journal of Nuclear Medicine*, 42, Proceedings of the 48th Annual Meeting, 193P (2001).

Wendt et al., "Correction of Scatter and Septal Penetration in Ho-166 Images to Enable Narrow Beam Attenuation Correction", *Journal of Nuclear medicine*, 43(5), 221P-222P (2002).

Winston, "Radioisotope Therapy in Bone and Joint Disease", *Seminars in Nuclear Medicine*, 9, 114-120 (1979).

Wiseman et al., "Bone Targeted Radioisotope Therapy for Treatment of Multiple Myeloma and Bone Tumors", *International Journal of Cancer*, 13, Abstract O 109, 104 (2002).

Wiseman et al., "Residual Whole Body 153Samarium Activity Predicts for Successful Autologous Peripheral Blood Progenitor Cell (PBPC) Engraftment Following High Dose 153Samarium Ethylene Diamine Tetramethylene Phosphonate (153Sm-EDTMP) Targeted Radiotherapy", *Blood*, 96, Abstract 1811, 421 (2000).

Young et al., "High Dose Samarium-153 Ethylenediaminetetramethylene Phosphate (SM-153 EDTMP) in the Treatment of Bone Sarcomas", *The Journal of Nuclear Medicine*, 40(5), Proceedings of the 46th Annual Meeting, 219P (1999).

Zeevaart et al., "Metal-ion Speciation in Blood Plasma Incorporating the Bisphosphonate, 1-hydroxy-4-aminopropilydenediphosphonate (APD), in Therapeutic Radiopharmaceuticals", *Journal of Inorganic Biochemistry*, 73, 265-272 (1999).

"Abstract Book, Annual Congress of the EANM", *European Journal of Nuclear Medicine and Molecular Imaging*, 31, Helsinki, 2004, Including abstracts P908, P925-P936, and P946-P952 (2004).

"Manufacture of Triethylene Tetramine", *Research Disclosure*, 315, No. 31591, 595 (1990).

Goldman, "Good Drug, Bad Luck: Business, Regulatory Issues Can Create Obstacles for Drug Development", *Journal of the National Cancer Institute*, 96, 1573-1574 (2004).

Kyle et al., "Multiple Myeloma", *The New England Journal of Medicine*, 351, 1860-1873 (2004).

"Communication pursuant to Article 96(2) EPC for corresponding European Patent Application No. 00944644.4", (May 2, 2007), 6 pgs.

Blumenthal, R. D., et al., "Use of Antioxidant Vitamins to Reduce Radioimmunotherapy-Induced Gastrointestinal and Hematopoietic Toxicity", *Proceedings of the 90th Annual Meeting of the American Association for Cancer Research*, vol. 40, (Abstract #4227), (Mar. 1999), p. 641.

Tofe, A. J., et al., "Antioxidant Stabilization of Bone Agents", *Radiopharmaceuticals II: Proceedings of the 2nd International Symposium on Radiopharmaceuticals*, (Mar. 19-22, 1979, Seattle, Washington), (1979) 637-644.

Tofe, A. J., et al., "Antioxidant Stabilization of Bone Agents", *American Journal of Roentgenology*, 132(3), (Abstract No. 42, International Symposium on Radiopharmaceuticals), (Mar. 1979), p. 493.

Tofe, A. J., et al., "In Vitro Stabilization of a Low-Tin Bone-Imaging Agent ($^{99m}$Tc-Sn-HEDP) by Ascorbic Acid", *Journal of Nuclear Medicine*, 17(9), (1976), 820-825.

* cited by examiner

HIGH DOSE RADIONUCLIDE COMPLEXES FOR BONE MARROW SUPPRESSION

RELATED APPLICATIONS

This application is a continuation of U.S. patent application Ser. No. 10/882,054, filed Jun. 30, 2004, entitled HIGH DOES RADIONUCLIDE COMPLEXES FOR BONE MARROW SUPPRESSION, which is a divisional of U.S. patent application Ser. No. 10/784,476, filed Feb. 23, 2004, now U.S. Pat No. 7,097,823 entitled HIGH DOSE RADIONUCLIDE COMPLEXES FOR BONE MARROW SUPPRESSION, which is a continuation application of U.S. patent application Ser. No. 10/159,245, filed May 29, 2002, now abandoned entitled HIGH DOSE RADIONUCLIDE COMPLEXES FOR BONE MARROW SUPPRESSION, which is a divisional application of U.S. patent application Ser. No. 10/014,335, filed Dec. 11, 2001, Now U.S. Pat. No. 6,767,531, Issued Jul. 27, 2004, entitled HIGH DOSE RADIONUCLIDE COMPLEXES FOR BONE MARROW SUPPRESSION, which is a continuation under 35 USC § 111(a) of PCT Application Serial No. PCT/US00/16052, filed on Jun. 12, 2000 and published as WO 00/76556 on Dec. 21, 2000, which claims priority from provisional U.S. Patent Application No. 60/139,065, filed Jun. 11, 1999, 60/143,780, filed Jul. 13, 1999 and 60/149,821, filed Aug. 19, 1999, all of which are incorporated herein by reference.

BACKGROUND OF THE INVENTION

The use of agents which cause partial or total suppression or eradication of bone marrow has become an accepted part of certain procedures used to treat patients with cancers such as leukemias, lymphomas, myelomas and Hodgkin's disease as well as in the treatment of patients suffering from hematopoietic disorders such as sickle cell anemia and thalassemia. In situations where the patient is suffering from a hematopoietic disorder such as thalassemia or sickle cell anemia, bone marrow transplantation may offer the possibility of a cure. If the abnormal bone marrow of an individual suffering from sickle cell anemia or thalassemia can be eradicated and then replaced with a bone marrow that takes and is reproduced and capable of producing normal red cells with normal hemoglobin, the individual may be cured.

Multiple myeloma is a disease of abnormal plasma cell proliferation that can result in anemia, pathologic fractures, renal failure, and death. Complete eradication of the abnormal plasma cells and precursor abnormal cells that may differentiate into abnormal plasma cells can prevent the progression, reverse or even cure the disease.

Current therapy is high dose chemotherapy (melphalan or combinations such as thiotepa/busulfan/cyclophosphamide) with or without total body irradiation (TBI). Treatment with melphalan 140 mg/m$^2$ of body-surface area given intravenously can induce complete remissions in about 20-30% of patients. However, it causes severe and sometimes irreversible myelosuppression. For example, see B. Barlogie et al., *Blood,* 72, 2015 (1989); (1998); D. Cunningham et al., *J. Clin. Oncol.,* 12, 764 (1994); R. Bataille et al., *New Engl. J. Med.,* 336, 1657 (1997).

Furthermore, when radiation is combined with other cytotoxic therapies, such as chemotherapy, the toxicity can be additive or synergistic. In addition, patients who undergo bone marrow suppression or ablation, sufficient to require either growth factor support, transfusion support or stem cell reinfusion, may encounter toxicities from the chemotherapy, from TBI, or both.

The dose of chemotherapy and radiotherapy that can be administered to an individual patient is often limited by patient age or overall health. Some patients who could benefit from high dose chemotherapy and radiotherapy do not receive it because they are considered to old or have other concomitant diseases which make them unsuitable candidates because of the non-target organ toxicity currently associated with these therapies. Higher doses of radiation may increase the percentage of tumor cells that are killed, and, with ionizing radiation, there comes a point where small increments in radiation can have a major impact on the percentage of cells killed.

The use of complexed radionuclides for bone marrow suppression is discussed in U.S. Pat. No. 4,853,209, where the use of Samarium-153 ($^{153}$Sm), Gadolinium-159 ($^{159}$Gd), or Holmium-166 ($^{166}$Ho) complexed with a ligand selected from ethylenediaminetetramethylenephosphonic acid (EDTMP), diethylenetriaminepentamethylenephosphonic acid (DTPMP), hydroxyethylethylenediaminetrimethylenephosphonic acid (HEEDTMP), nitrilotrimethylenephosphonic acid (NTMP), or tris(2-aminoethyl)amine-hexamethylenephosphonic acid (TTHMP) is disclosed. Phosphonic acid-containing chelators are selected due to their ability to target the radionuclide to the bone.

U.S. Pat. Nos. 4,882,142, and 5,059,412 are directed to a method for the suppression of bone marrow and to a composition for use in the method. The method comprises administering to a mammal in need of such treatment a bone marrow suppressing amount of at least one composition comprised of a radionuclide $^{153}$Sm, $^{159}$Gd, or $^{166}$Ho complexed with 1,4,7,10-tetraazacyclododecanemethyl-enephosphonic acid as the macrocyclic chelating moiety. The method of bone marrow suppression described therein may be used in combination with chemotherapeutic drugs and/or external radiation. The compositions comprise the radionuclides in dosages comprising from about 18 to 1850 megabecquerels per kilogram of body weight of the target mammal. The amount of radioactivity delivered to the bone is necessarily lower, and was not determined.

Therefore, a continuing need exists for methodologies and agents useful for selective bone marrow suppression and/or for adequate tumor cell killing, that is, wherein the bone marrow is suppressed and/or tumor cells killed with only minimal damage to non-target soft tissues, for example, liver, urinary bladder, and kidney. There is also a need for a means of delivering high radiation doses to sites of disease in or near bone, with standard or high dose chemotherapy without increasing toxicity to non-target organs. For those situations where bone marrow support can aid in therapy or cure, it would be desirable to have a means of first selectively suppressing the abnormal or diseased bone marrow independent of, or with limited, total body irradiation.

SUMMARY OF THE INVENTION

The present invention provides a method for selectively, rapidly, and effectively suppressing bone marrow or to treat a pathology associated with (in or near) the bone or bone marrow. In one aspect, the method comprises administering to a mammal in need of such treatment a high dosage of a complex of a bone marrow suppressing radionuclide with a bone targeting ligand, such as an aminophosphonic acid. Such pathologies include cancer, autoimmune diseases, certain infections and certain hematopoietic genetic disorders.

Preferably, the radionuclide is $^{166}$Ho and the ligand is a macrocyclic aminophosphonic acid such as DOTMP. The complex is preferably administered in a single treatment dose effective to deliver at least 20 Gy to the bone marrow of the subject. The present invention also provides aqueous compositions comprising $^{166}$Ho-DOTMP and a radioprotectant that are stable for at least about 72 hours under ambient conditions.

A preferred embodiment of the invention provides a method to increase the efficacy of chemotherapy, particularly high dose or intensive chemotherapy, without a substantial increase in total side effects, and more preferably, without the need for TBI. This method comprises administering an effective bone marrow suppressing amount of a radionuclide-amino phosphonate complex to a subject in need of such treatment in conjunction with one or more chemotherapeutic agents, while maintaining an acceptable level of tolerance of the subject to the total therapeutic regimen. For example, it has been unexpectedly found that a high dosage of radiation can be delivered to the bone marrow of a subject afflicted with a bone-associated neoplasm (cancer) or non-cancerous myeloproliferative disorder in conjunction with high dose chemotherapy, such as melphalan in the case of myeloma, while not substantially increasing the side effects as compared to the side effects associated with the high dose chemotherapy alone.

For example, the use of at least about 200 mg/m$^2$ melphalan to treat multiple myeloma can be combined with a dosage of a $^{166}$Ho aminophosphonate complex effective to deliver about 20-60 Gy, preferably about 30-50 Gy, to the bone marrow of the afflicted subject without substantially increasing the side effects over those associated with melphalan therapy alone at about 140 mg/m$^2$ or about 200 mg/m$^2$. Such treatment has the advantage of providing efficacy comparable to that obtained from treatment with a combination of melphalan and TBI, without the side effects associated with TBI.

The efficacy of conventional melphalan therapy (i.e., 70-120 mg/m$^2$ can also be enhanced by administration of the present complexes, thus improving the outcome for older patients. Therefore, the efficacy of current treatment regimens to treat multiple myeloma, e.g., 140 mg/m$^2$ melphalan plus TBI or 200 mg/m$^2$ melphalan alone, can be substantially enhanced without substantial increase in side effects, e.g., those due to melphalan and/or TBI used without the complex.

The preferred radionuclide compositions employed in the method of the present invention are capable of delivering a significant portion, preferably greater than about 15%, e.g., about 25-35% of the radioactivity present in the composition to bone tissue while not deleteriously affecting non-target soft tissues. Therefore, for those disease states where the treatment regimen requires bone marrow suppression, the present invention is particularly advantageous since it provides a means of achieving selective reduction in the hemopoietic cell population, without having to resort to external irradiation of the subject, e.g., to TBI, resulting in minimal damage to non-target tissues. The reduction in the radiation dose delivered to non-target tissues (as compared to the use of TBI alone), provides the opportunity to use the same or increased amounts of conventional chemotherapeutic regimens, particularly non-radioactive antineoplastic ("anti-cancer") agents that per se suppress bone marrow, such as alkylating agents.

It may be possible to completely eliminate the use of targeted radiation or TBI in certain patient populations, such as those under 55 years of age, while retaining equivalent efficacy. It may also be possible to increase the efficacy of regimens in which TBI is desirable, but too hazardous to use, as in older patients (>55 years of age). However, if it is desirable to employ targeted irradiation or TBI in conjunction with the bone marrow suppression method described herein, for example, in the treatment of leukemia, it can be possible to reduce the radiation dosage used for the total body irradiation and still obtain the same or higher level of reduction of leukemic cells.

Preferred radionuclide complexes comprise radionuclides that exhibit half-lives of sufficient length so that they can deliver preselected high doses of radiation after bone-targeting and soft tissue clearance, but which exhibit half-lives sufficiently short so that they decay in a relatively short time to allow safe bone marrow or stem cell transplantation or other therapy. For example, $^{166}$Ho has an energetic beta-particle with a long path length. Yet, despite increasing the dose of $^{166}$Ho from about 20 Gy to about 50 Gy to the marrow along with moderately high or very high doses of chemotherapy, there has been surprisingly no increase in toxicity to other organs beyond that expected from the chemotherapy itself and, surprisingly, no evidence of delay or difficulty in engraftment of marrow or stem cell transplant due to direct toxicity to the bone marrow space. The rapid radioactive decay also unexpectedly permits subsequent use of high dose chemotherapy, since cumulative effects are avoided or lessened. Thus, the present method provides the basis for a potent combination therapy, particularly with respect to cancers that are associated with bone, because additive toxic side effects are readily avoided.

In one aspect of the invention, the complex of the macrocyclic aminophosphonic acid, 1,4,7,10-tetraazacyclododecane, and $^{166}$Ho was found to deliver higher doses of radiation to the bone or to adjacent areas than previously thought possible, without undue deleterious side effects. A preferred ratio of DOTMP to $^{166}$Ho is above 3; preferably about 3.5-5, most preferably about 3.5.

Furthermore, it was unexpectedly found that bone marrow can be ablated effectively with a single dose or with closely spaced dosing regimens, further reducing the handler's exposure to radiation. As used herein, the term "single dosage" or "single dose" means that the total dosage of radionuclide complex is administered in one (1) or more doses within a short period of time, e.g., less than about 24 hours. Preferably the doses will be administered within about 12 hours, more preferably within about 8 hours. Most preferably the doses will be administered within about 0.1-4 hours. Preferably the dose will be also administered as a single infusion or injection.

Preferably, an effective bone marrow suppressing dose of a radionuclide aminophosphonic acid complex, such as $^{166}$Ho-DOTMP will administer a total dose of 20-60 Gy, preferably about 30-50 Gy and, most preferably, about 37-45 Gy of radiation to the bone/bone marrow of the subject. At about 30% uptake, e.g., for a human subject, total therapy dose to bone marrow is about 500-4000 mCi (about 18.5-148 GBq).

Because the actual percentage of the administered dose of radiation that reaches the bone/bone marrow necessarily varies from subject to subject, the present method also preferably comprises the steps of first administering a dose (the "diagnostic or dosimetry dose") of a radionuclide complex effective to determine the dosage required to subsequently deliver an effective therapy dose or doses, and then determining the percent uptake of the diagnostic or dosimetry dose by the bone of the subject, e.g., via whole body retention measurements. Although a radionuclide other than the intended therapeutic radionuclide can be used for dosimetry measurements, it is preferable to use the same radionuclide for dosimetry measurements and for therapy.

The administered dosage can, in some cases where patients have relatively low uptake in the skeleton, contain from about 2000 to about 2750 megabecquerels (MBq) per kilogram of body weight of said mammal. The most preferred dosage contains from about 2000 to about 2500 megabecquerels per kilogram of body weight of said mammal.

The dosing is preferably accomplished with a radionuclide complex emitting a beta energy of >0.5 MeV and having a radionuclide half-life of less than 5 days, most preferably <3 days, at a beta energy of >1 MeV. Preferred radionuclides include radionuclides selected from the group consisting of $^{153}$Sm, $^{90}$Y, $^{159}$Gd, $^{186}$Re, $^{188}$Re, and $^{166}$Ho (half-life 26.8 hr.) complexed with a bone targeting complexing ligand.

The radionuclide complexes can be administered alone or in combination with adjuvant bioactive agents, that act in conjunction with the localized complex in order to treat diseases, such as disease or pathologies associated with (at or near) mammalian bone (including bone marrow and associated tissue or cells). Such agents include antineoplastic chemotherapeutic agents known to the art. The complex can be delivered at a dose that itself is effective without the use of a chemotherapeutic agent or irradiation from an external source. Such regimens are particularly effective to treat cancers such as leukemia, myeloma, metastatic breast or metastatic prostate cancer, Hodgkin's lymphoma, osteosarcoma, Ewing's sarcoma or Paget's disease.

Following treatment with an amount of the present complexes, and, optionally, with external irradiation, growth factor support, chemotherapy, hormone therapy, or immunosuppressive therapy, the subject's bone marrow can be augmented by blood marrow restoration, or regenerated, as by transplantation with purged autologous or matched allogeneic bone marrow (including peripheral blood stem cells), and/or by treatment with bone marrow-stimulating agents.

The preferred chelating agents useful for practicing the present invention are polyaminophosphonic acid chelators, such as, for example, ethylenediaminetetramethylenephosphonic acid (EDTMP), diethylenetriaminepentamethylenephosphonic acid (DTPMP), hydroxyethylethylenediaminetrimethylenephosphonic acid (HEEDTMP), nitrilotrimethylenephosphonic acid (NTMP), 1,4,7,10-tetraazacyclododecanetetramethylenephosphonic acid (DOTMP), tris(2-aminoethyl)aminehexamethylenephosphonic acid (TTHMP), 1-carboxyethylenediamine-tetramethylenephosphonic acid (CEDTMP), hydroxyethylidene diphosphonate (HEDP), bis(aminoethylpiperazine)tetramethylenephosphonic acid (AEPTMP), N-methylethylenediaminetrimethylenephosphonic acid (MEDTMP), N-isopropylethylenediaminetriemthylenephosphonic acid (IEDTMP), N-benzylethylenediaminetrimethylenephosphonic acid (BzEDTMP), methylene diphosphonate, hydroxymethylene diphosphonate, ethane-1-hydroxy-1,1-diphosphonic acid, and the like. Other useful chelating agents for radionuclides are generally disclosed in U.S. Pat. Nos. 5,059,412, 5,066,478, 5,300,279 and 4,897,254.

Preferred macrocyclic aminophosphonic acids are of the structure:

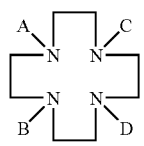

wherein substituents A, B, C, and D are independently selected from hydrogen, hydrocarbon radicals having from 1-8 carbon atoms,

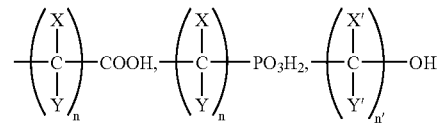

and physiologically acceptable salts of the acid radicals wherein X and Y are independently selected from the group consisting of hydrogen, hydroxyl, carboxyl, phosphonic, and hydrocarbon radicals having from 1-8 carbon atoms and physiologically acceptable salts of the acid radicals, and n is 1-3 with the proviso that when n>1, each X and Y may be the same as or different from the X and Y of any other carbon atom; X' and Y' are independently hydrogen, methyl, or ethyl radicals, and n' is 2 or 3, with the proviso that at least two of said nitrogen substituents is a phosphorus containing group, i.e., wherein N and P are connected by alkylene or substituted alkylene.

A more preferred macrocyclic aminophosphonic acid ligand is 1,4,7,10-tetraazacyclododecanetetramethylenephosphonic acid (DOTMP). See, e.g., U.S. Pat. Nos. 4,973,333 and 5,714,604.

The present method can also be employed to treat pathologies other than cancer associated with (at or near) mammalian bone, that can be ameliorated by partial bone marrow suppression or by complete bone marrow ablation followed by bone marrow transplantation. The treatment can be accomplished by delivering i.e., 250-3000 megabecquerels per kg of body weight of the complex to the subject to be treated. Such pathologies include, but are not limited to, immunological disorders such as autoimmune diseases, e.g., Crohn's disease, rheumatoid arthritis or multiple sclerosis; metabolic diseases, such as osteoporosis or osteopenia; infections and infectious disease such as tuberculosis or blastomycoses, inflammatory diseases such as osteomyelitis or Paget's disease; hematopoietic disorders, and conditions treatable with stem cell transplantation, with or without gene therapy, that utilize bone marrow ablation, such as sickle cell anemia and lysosomal and peroxisomal storage diseases.

The present invention also provides novel liquid compositions, preferably aqueous compositions, comprising $^{166}$Ho-DOTMP combined with an effective stabilizing amount of ascorbic acid, gentisic acid, or other radio-stable stabilizing agent buffered to pH 7-8, as well as methods for preparing the compositions. The ascorbic acid, gentisic acid, and the like, maintain the radionuclide complex stability and reduces the amount of free radionuclide delivered in vivo. For example, ascorbic acid or gentisic acid may be present in the unit dosage forms useful in the practice of the present invention at about 35-75 mg/ml of composition. Stabilization unexpectedly inhibits radiolytic degradation of the complexes, i.e., so high (300 mCi/ml (12 GBq/ml)) levels of $^{166}$Ho-DOTMP can be maintained in the dosage forms, and thus allows distribution to hospitals at high levels of purity, with high levels of $^{166}$Ho-DOTMP.

DETAILED DESCRIPTION OF THE INVENTION

Figure 1:
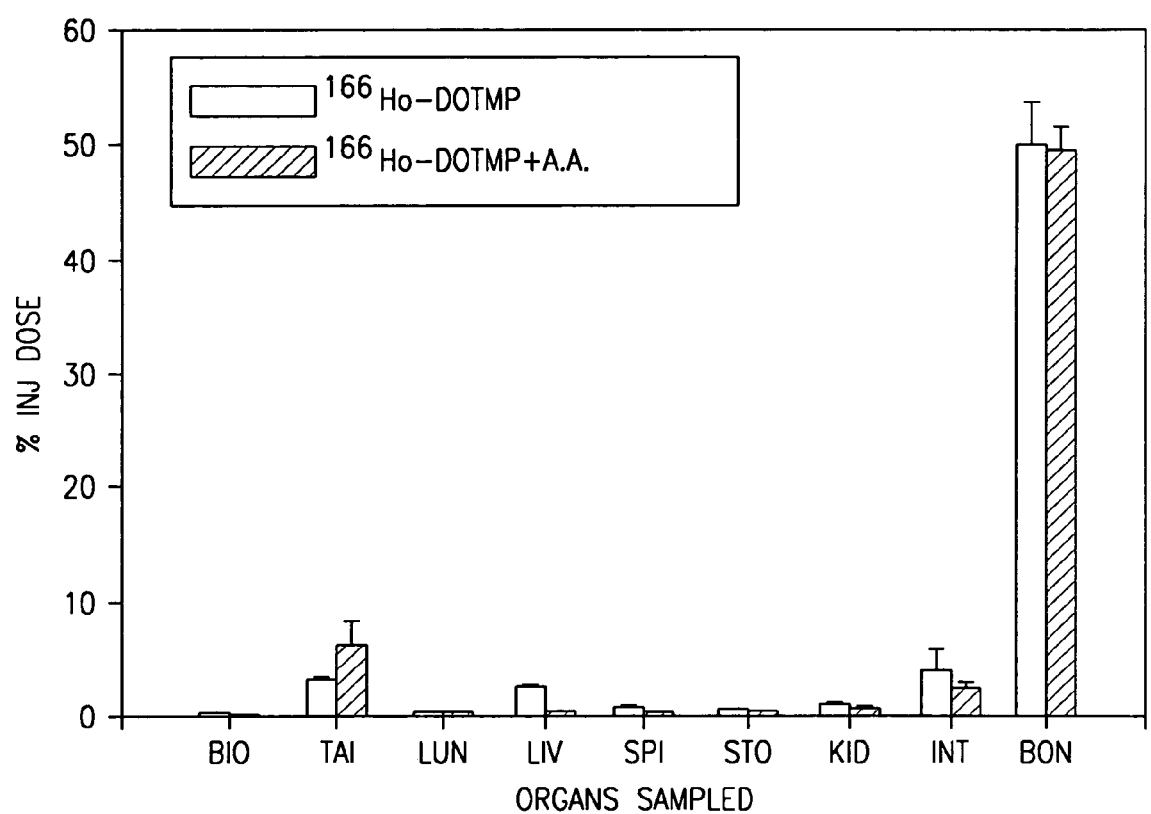
FIG. 1 is a graphical representation of the uptake of $^{166}$Ho-DOTMP in bones and non-target organs.

As used herein, the term "mammal" means a warm blooded mammal, including humans, and is meant to encompass mammals in need of bone marrow suppression, especially humans; thus in some instances the term "patient" or "subject" is alternatively used for mammal.

The term "disease" includes pathologies and deleterious conditions, such as inflammatory responses, cancer, autoimmune, and genetic disorders.

The term "bone marrow restoration" includes partial or complete regeneration or augmentation of the bone marrow by marrow transplantation or hematopoietic stem cell transplantation and/or stimulation of bone marrow regeneration by administration of growth factors such as cytokines, glycoproteins and the like.

As used herein, the term "bone marrow transplant (BMT)" includes autologous, allogenic, xenogeneic marrow transplantation and stem cell transplantation.

The term "bone marrow suppression" refers to partial or essentially total eradication ("ablation" or "myeloablation") of the bone marrow, in particular a temporary or permanent reduction of the hemopoietic stem cell population.

A sub-ablative therapy is one that does not completely eradicate bone marrow, e.g., the marrow may recover, particularly if hematopoietic cell growth factors are administered.

As used herein, the term that external irradiation (targeted or TBI) is not used "in conjunction with" the radionuclide complex and, optionally, chemotherapy, is intended to mean that external irradiation is not employed as part of the same treatment protocol. For example, a patient could have received external radiation treatment as part of a previous treatment protocol and still be considered not to have received external radiation "in conjunction with" treatment with the radionuclide complex. Thus, the term "inconjunction with" is intended to mean administration as part of the same protocol radionuclide complex, in order to accomplish the recited therapeutic effect, e.g., bone marrow suppression.

As used herein, the term "substantial" when used with respect to the side effects of chemotherapy or radiation therapy is to be understood by reference to the art-recognized definitions and scales employed in the working examples.

As used herein, the term "high dose" refers to a dose that is in the upper range of the dose used in conventional therapy to treat a particular pathology, as recognized by the art. As defined in Example 10, this can include the MTD±10%. The dose range and highest typical dose for certain chemotherapeutic agents is given herein below for illustration.

The present invention is directed to compositions and methods for suppressing bone marrow and/or treating a disease in or near the bone or bone marrow that is ameliorated by said suppression. The present invention has significant benefits in that it permits rapid and selective bone marrow suppression (the bone marrow can be suppressed with only minimal damage to non-target soft tissues, such as, for example, lung, liver, stomach, mucosal linings and the like) without the need for sustained exposure to radiation or for exposure to a large, >about 15-20:1, molar ratio of chelating agent to radionuclide. The complexes of the invention can also be administered prophylatically or in an adjuvant setting with little evidence of disease but likelihood of recurrence from minimal disease presence, e.g., to minimize the probability of metastases of established cancer.

As will be more fully discussed later herein, the properties of the radionuclide, and of the radionuclide aminophosphonic acid complex are important considerations in determining which radionuclide composition should be employed for any particular treatment. For the purpose of convenience, the radionuclide aminophosphonic acid compositions will frequently be referred to as "radionuclide complexes or compositions" and the aminophosphonic acid derivative referred to as the "ligand," "chelator," or "chelating agent". The term "complexes" or "compositions" includes both the free compounds and the pharmaceutically acceptable salts thereof.

Radionuclides

It is important that the half-life of the complexed radionuclides be sufficiently long to allow for localization and delivery of the complex in the bone tissue via binding to chelator while still retaining sufficient radioactivity to accomplish essentially total bone marrow suppression or eradication. The half-life also should be relatively short, so that after bone marrow irradiation is achieved, it is possible to proceed with bone marrow or stem cell transplantation with minimal delay prior to transplant, and in order to enhance the prospects of bone marrow engraftment and patient recovery. Generally, it is preferred to use a radionuclide complex that results in rapid biolocalization of the radionuclide in the bone tissue so as to achieve rapid onset of bone marrow irradiation. It is also beneficial to use a radionuclide having sufficient beta energy, such that substantially all bone marrow cells receive a toxic irradiation from the targeted bone surfaces.

For example, radionuclides useful for bone marrow ablation can exhibit beta energy >0.5 MeV, preferably >1 MeV with an effective half-life of about <5 days, preferably <3 days. Certain radionuclides such as Sr-89 have been demonstrated, when selectively deposited in bone, to suppress bone marrow. [See, for example, Y. Shibata et al., *J. Leukocyte Biol.*, 38, 659 (1985).] However, this compound is not clinically useful for this purpose since the long half-life of Sr-89 (50 days) prevents transplantation of the new marrow for an unacceptable period of time. Radionuclides useful in the method and compositions of this invention are Arsenic-77 ($^{77}$As), Molybdenum-99 ($^{99}$Mo), Rhodium-105 ($^{105}$Rh), Lutetium-177 ($^{177}$Lu), Cadmium-115 ($^{115}$Cd), Antimony-122 ($^{122}$Sb), Promethium-149 ($^{149}$Pr), Osmium-193 ($^{193}$Os), Gold-198 ($^{198}$Au), Thorium-200 ($^{200}$Th); preferably Samarium-153 ($^{153}$Sm), Yttrium-90 ($^{90}$Y), Gadolinium-159 ($^{159}$Gd), Rhenium-186 ($^{186}$Re), Rhenium-188 ($^{188}$Re), and Holmium-166 ($^{166}$Ho). Especially preferred is $^{166}$Ho, which emits high energy beta particles and gamma radiation (80 KeV, 6.0%) useful for imaging and exhibits a half-life of 26.8 hr.

The respective radionuclides can be obtained using procedures well known in the art. Typically, the desired radionuclide can be prepared by irradiating an appropriate target, such as a metal, metal oxide, or salt. Another method of obtaining radionuclides is by bombarding nuclides with particles in a linear accelerator or cyclotron. Yet another way of obtaining radionuclides is to isolate them from fission product mixtures. The method of obtaining the radionuclide is not critical.

Chelating Agents

Aminophosphonic acids, particularly macrocyclic aminophosphonic acids, are the ligands of choice as chelators for the radionuclides useful in the present methods. These compounds can be prepared by a number of known synthetic techniques. Generally, a compound containing at least one reactive amine hydrogen is reacted with a carbonyl compound (aldehyde or ketone) and a phosphorous acid or appropriate derivative thereof.

Methods for carboxyalkylating macrocyclic amines to give amine derivatives containing a carboxylalkyl group are disclosed in U.S. Pat. No. 3,726,912. Methods to prepare alkylphosphonic acid amines and hydroxyalkylamines are disclosed in U.S. Pat. No. 3,398,198. See also, U.S. Pat. No. 5,066,478 and 5,300,279.

The amine precursor (1,4,7,10-tetraazacyclododecane) employed in making certain of the macrocyclic aminophosphonic acids is a commercially available material. The preparation of the macrocyclic aminophosphonic ligand of this invention can also be found U.S. Pat. No. 5,059,412 entitled "Macrocyclic Aminophosphonic Acid Treatment of Calcific Tumors"; by Simon et al., the disclosure of which is hereby incorporated by reference.

The preparation of these ligands have been described in several U.S. Patents such as, U.S. Pat. Nos. 4,973,333, 4,882,142, 4,853,209, 4,898,724, 4,897,254, 5,587,451, 5,714,604, 5,064,633, 5,587,451, 5,066,478, 5,300,279, 5,059,412, and 5,064,633. The preferred ligands useful for practicing the present invention are selected from the group consisting of ethylenediaminetetramethylenephosphonic acid (EDTMP), diethylenetriaminepentamethylenephosphonic acid (DTPMP), hydroxyethylethylenediaminetrimethylenephosphonic acid (HEEDTMP), nitrilotrimethylenephosphonic acid (NTMP), 1,4,7,10-tetraazacyclododecanetetramethylenephosphonic acid (DOTMP), tris(2-aminoethyl)aminehexamethylenephosphonic acid (TTHMP), methylene diphosphonate, hydroxymethylene diphosphonate, hydroxyethylidene diphosphonate (HEDP); and ethane-1-hydroxy-1,1-diphosphonic acid. Preferred ligands are macrocyclic aminophosphonic acid ligands of which 1,4,7,10-tetraazacyclododecanetetramethylenephosphonic acid (DOTMP) is an example. The present invention includes the use of the bone marrow suppressing method and composition in combination with other drugs and/or radiation sources.

Radionuclide Complexes

Radionuclide complexes suitable for use in the present invention must have particular properties to be suitable as therapeutic agents. The radionuclide complex must be taken up preferentially by bone so that it is possible to deliver a bone marrow suppressing dose of radiation to the bone marrow with minimal exposure to other tissues such as lung, liver, bladder or kidneys. The radionuclide complex also should be rapidly taken up by bone and rapidly cleared from the blood, thereby further reducing exposure to non-target tissues.

The radionuclide and ligand can be combined under any conditions that allow the two to form a complex. Generally, mixing in water at a controlled pH (the choice of pH is dependent upon the choice of ligand and radionuclide) is all that is required. The complex is formed by chelation of the radionuclide by an electron donor group or groups that results in a relatively stable radionuclide complex, e.g., stable to the disassociation of the radionuclide from the ligand. For example, $^{166}$Ho-DOTMP is formed by adding a $^{166}$Ho salt, such as the chloride or nitrate in aqueous HCl (0.1-1N), to a sterile, evacuated vial containing at least 3 equivalents of DOTMP in aqueous base (KOH, NaOH and the like). After stirring at a pH=10.5, the pH is then adjusted to 7-8 by adding phosphate buffer and a stabilizing agent such as ascorbic acid. Complexation of >99% is achieved.

For the purpose of the present invention, bone marrow suppressing radionuclide compositions described herein and physiologically acceptable salts thereof are considered equivalent. Physiologically acceptable salts refer to the acid addition salts of those bases which will form a salt with at least one acid group of the ligand or ligands employed and which will not cause significant adverse physiological effects when administered as described herein. Suitable bases include, for example, the alkali metal and alkaline earth metal hydroxides, carbonates, and bicarbonates such as, for example, sodium hydroxide, potassium hydroxide, calcium hydroxide, potassium carbonate, sodium bicarbonate, magnesium carbonate and the like, amine hydroxides, carbonates, and bicarbonates such as, for example, ammonium hydroxide, ammonium carbonate, and the like, or primary secondary and tertiary amine hydroxides, carbonates, and bicarbonates such as, for example, trimethyl ammonium carbonate and the like. Physiologically acceptable salts can be prepared by treating the macrocyclic aminophosphonic acid with an appropriate base.

The macrocyclic aminophosphonic acid complexes when formed at approximately a ligand to metal molar ratio of 1:1 to 20:1 give biodistributions that are consistent with those exhibited by known agents that are bone-specific. The preferred bone marrow suppressing radionuclide composition utilizes $^{166}$Ho with DOTMP. Preferably, molar ratios of DOTMP to $^{166}$Ho are above 3, e.g., 3.5-5:1. The most preferred ratio is about 3.5:1. Such ratio provides adequate complexation of the radionuclide while compensating for radiolysis of the ligand. Lower ratios of DOTMP to $^{166}$Ho are unstable in vivo and not therapeutically effective. By contrast, other acyclic aminophosphonic acid complexes can result in substantial localization of radioactivity in soft tissue (e.g., liver) if large excess amounts of ligand are not used. Large excesses of ligand are undesirable since uncomplexed ligand may be toxic to the patient or may result in cardiac arrest or hypocalcemic convulsions. In addition, the macrocyclic aminophosphonic acid ligands are useful when large amounts of metal are required (i.e. for metals that have a low specific activity). In this case, the macrocyclic aminophosphonic acid ligands have the ability to deposit more tolerable doses of radioactivity in the bone than is possible when using non-cyclic aminophosphonic acid ligands.

Stabilizing Agents

A pharmaceutically acceptable means of protecting the radionuclide complex from radiolytic decay of the chelator is highly preferred. Preferred radioprotectants of the present invention are radio-stable anti-oxidants, compounds that either reduce the number or the activity of oxidizing radicals. Exemplary radioprotectants that can be employed in the practice of the present invention are ascorbic acid, gentisic acid, nicotinic acid, ascorbyl palmitate, HOP(:O)H$_2$, monthioglycerol, sodium formaldehyde sulfoxylate, Na$_2$S$_2$O$_5$, Na$_2$S$_2$O$_3$, SO$_2$, or a reducing agent combined with BHA, BHT, pyrogallate or tocopherol and the like. Ascorbic acid is the preferred radioprotectant for use in the practice of the present invention, and can be used at about 35-75 mg/mL of liquid composition. This concentration of ascorbate can provide a solution of $^{166}$Ho-DOTMP that is stable, e.g., therapeutically useful, for at last 72 hours, at ambient conditions, e.g., unfrozen.

The formulations of the present invention are in the solid or preferably liquid form containing the active radionuclide complexed with the ligand. These formulations can be in kit form such that the chelator and radionuclide are mixed at the appropriate time prior to use in a suitable liquid carrier with the radioprotectant. Whether premixed or as a kit, the formulations usually require a pharmaceutically acceptable carrier, such as water.

Pharmaceutical Dosage Forms

The pharmaceutical dosage forms suitable for injection or infusion can include sterile solutions, dispersions, emulsions, or microemulsions, comprising the active ingredient which are adapted for the extemporaneous preparation of sterile injectable or infusible solutions or dispersions, optionally encapsulated in protective matrices such as nanoparticles or microparticles. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), DMSO, and suitable mixtures thereof. In many cases, it will be preferable to include isotonic agents, for example, sugars, buffers or sodium chloride.

Injectable suspensions as compositions of the present invention require a liquid suspending medium, with or without adjuvants, as a carrier. The suspending medium can be, for example, aqueous polyvinylpyrrolidone, inert oils such as vegetable oils or highly refined mineral oils, or aqueous carboxymethylcellulose solutions. If necessary to keep the complex in suspension, suitable physiologically acceptable adjuvants can be chosen from among thickeners such as, for example, carboxymethylcellulose, polyvinylpyrrolidone, gelatin, and the alginates. Many surfactants are also useful as suspending agents, for example, lecithin, alkylphenol, polyethylene oxide adducts, naphthalenesulfonates, alkylbenzenesulfonates, and the polyoxyethylene sorbitan esters. Many substances that effect the hydrophobicity, density, and surface tension of the liquid suspension medium can assist in making injectable suspensions in individual cases. For example, silicone antifoams, sorbitol, and sugars are all useful suspending agents.

Dosages of the Radionuclide Complexes

The "bone-marrow suppressing amount" or other effective therapeutic amount of radionuclide composition administered to achieve bone marrow suppression will vary according to factors such as the age, weight and health of the patient, the disease state being treated, the treatment regimen selected, as well as the nature of the particular radionuclide composition to be administered. For example, less activity will be needed for radionuclides with longer half lives. The energy of the emissions will also be a factor in determining the amount of activity necessary. Preferably, a total dose of about 20-60 Gy, most preferably about 30-60 Gy, e.g., 40-50 Gy of radiation will be delivered to bone marrow via bone localization.

The radiation exposure is reported using the Grey scale (Gy) and is typically determined using a diagnostic dose of about 1200-2000 MBq (about 30 mCi to about 50 mCi) of the radionuclide/ligand. Determination of the doses of radiation delivered by the present complexes can be determined in accord with the methodologies of M. Bardies et al., *Physics in Medicine and Biology*, 41, 1941 (1996); J. Bayouth, *Radiation Physics*, University of Texas—Houston Graduate School of Biomedical Science: 111 (1993); A. H. Beddoe et al., *Physics in Medicine & Biology*, 21, 589 (1976); R. Bigler et al., *Health Physics*, 31, 213 (1976); R. Champlin et al., *Semin. Hematol*, 24, 55 (1987); R. E. Champlin et al., *Cancer Treatment Reports*, 68, 145 (1984); K. Eckerman et al., *Journal of Nuclear Medicine*, 35, 112P (1994); T. E. Hiu et al., *Proceedings of International Conference on Radiation Dosimetry and Safety*, Taipei, Taiwan, American Nuclear Society (1987); *I.C.R.P Report of the task group on reference man: anatomical, physiological and metabolic characteristics*. New York, Pergamon Press (1973); R. L. Loevinger et al., *MIRD Primer for Absorbed Dose Calculations*, New York, Society of Nuclear Medicine (1991); F. W. Spiers et al., *British Journal of Radiology*, 54, 500 (1981); S. R. Thomas et al., *J. Nucl. Med.*, 35, 73 (1994)," *Journal of Nuclear Medicine*, 33, 783 (1992).

Table 1 indicates the dosage levels achieved at various levels of skeletal uptake of the radionuclide.

TABLE 1

DOSAGE LEVELS AT PERCENT SKELETAL UPTAKE
Dose Level vs. Dose Required in MBq/kg[1]

| Dose Level | 15% Uptake | 30% Uptake | 45% Uptake |
|---|---|---|---|
| 20 Gy | 1110 | 518 | 370 |
| 30 Gy | 1665 | 777 | 555 |
| 40 Gy | 2220 | 1036 | 740 |
| 50 Gy | 2775 | 1295 | 925 |

[1]Average skeletal uptake in patients is about 30%.

The radiation amounts herein are reported in megabecquerels (MBq), Gy, or in mCi. The conversion between mCi and MBq for an average patient is illustrated below:

22.0 mCi/kg×70 kg×37 MBq/mCi=56,980 MBq (or 814 MBq/kg).

wherein 70 kg is used as an average patient weight. Herein both terms have been used. A becquerel is 1 disintegration per minute (dpm).

The mean absorbed dose to a target tissue from activity within a source organ for $^{166}$Ho and other radionuclide can be calculated using the general method defined by the Medical Internal Radiation Dose (MIRD) committee of the Society of Nuclear Medicine. The MIRD organ scale formalism simplifies this relationship for a radiation source in trabecular bone irradiating bone marrow to:

$$\overline{D} = \tilde{A} \cdot S(BM \leftarrow TB) \qquad \text{Equation 1}$$

Where:

$$S(BM \leftarrow TB) = \sum_i \Phi_i(BM \leftarrow TB) \cdot \Delta_i \qquad \text{Equation 2}$$

and:

$$\Phi_i(BM \leftarrow TB) = \frac{\phi(BM \leftarrow TB)}{m_{BM}} \qquad \text{Equation 3}$$

Where:
$\overline{D}$=Mean absorbed dose to the target organ of mass m
$\tilde{A}$=Total number of radioactive transitions within the source organ $n_i \cdot E_i = \Delta_i$=Amount of energy released per transition per specific radiation
$\phi_i(T \leftarrow S)$=Fraction of energy emitted from source organ absorbed in target organ for the specific radiation
$m_{BM}$=Mass of bone marrow
S(BM←TB)=S-value for trabecular bone surfaces irradiating adjacent bone marrow.

The distribution of radioactive material are calculated from whole body gamma camera emission images of $^{66}$Ho-DOTMP, and the rate of clearance from the skeleton will be measured from whole body retention data from $^{166}$Ho-DOTMP. S-values were generated for the Standard Man Phantom as defined by ICRP 23 using the revised bone and bone marrow model included in the software package MIRDOSE 3.1, and all values of radiation dose to bone marrow are calculated using this package. The calculation of residence time of $^{166}$Ho, is important, since from the residence time, the cumulated activity or Ã can be determined. Ã and S-values are then used to calculate absorbed dose (cGy/mCi) to the active bone marrow (Equation 1).

Independent methods can be used to estimate the total amount of skeletal radioactivity and its rate of disappearance from the skeleton, including gamma camera serial whole body imaging, external probe whole body retention measurements, and gamma counter counting of cumulative urine interval samples acquired 24 or 48 hrs. after injection.

More specifically, the following data for the calculations described herein should be obtained:
1. Whole body serial quantitative $^{166}$Ho-DOTMP diagnostic test dose scans over 24 hr to assess DOTMP pharmacokinetics and bio-distribution;
2. Cumulative urine collection and background subtracted whole body probe measurements over 48 hr; and
3. Serial whole blood sampling over 24 hr (10, 30 min, 1, 2, 4, and 24 hr).

Absorbed dose to the bone marrow is estimated by extrapolating late whole body clearance curve time points (>12 hr) back to time=0 to make an estimate of initial bone uptake and rate of clearance for further calculation of bone residence time and cumulated activity. If activity within the total body at greater than 12 hr is due to skeletal activity only, then the later time points for the whole body retention curve calculated from the serial probe and cumulative urine measurements can be used to extrapolate the initial skeletal uptake (PID(t=0)). The rate of skeletal clearance based ($T_{1/2 Effective}$) upon a mono-exponential function from which skeletal residence time can be determined. Total skeletal residence time (RT) is calculated using equation 4.

$$\text{Skeletal } RT = 1.44 \cdot PID(t=0) \cdot T_{1/2}^{Effective} \quad \text{Equation 4}$$

The total residence time is assumed to be distributed equally between cortical and trabecular bone surfaces (ICRP 1973). Once the residence times are calculated, the therapy dose of $^{166}$Ho are determined using Equation 5:

$$^{166}Ho - DOTMP \text{ therapy dose } (mCi) = \frac{\text{projected therapy dose } (cGy)}{\text{marrow dose } (cGy/mCi)} \quad \text{Equation 5}$$

The above calculations can be combined with methods for soft tissue dosimetry, to minimize the does to non-target tissues such as the urinary bladder wall.

The results of patients treated with 20 30 and 40 Gy with 140 mg/mL and 200 mg/m$^2$ are given in Example 11.

As discussed above, and exemplified below, the administered dose of radiation can be calculated by pre-administration of a diagnostic dose of a radionuclide complex. Depending on the percent bone uptake of a given radionuclide complex by a given subject, which is generally in the range of about 15 to about 45%, the range of activity per administered dose can generally be from about 250 to about 3000 megabecquerels per kilogram of body weight of said mammal. If uptake is low, or if a very high dose is desired, a dose of from about 750 to about 2500 megabecquerels per kilogram of body weight of said mammal, or from about 1000 to about 2000 megabecquerels per kilogram of body weight of said mammal may be prefered The effective amount used to obtain bone marrow suppression will typically be administered, generally by administration into the bloodstream, in a single or multi-dose infusion.

Bone Marrow Transplantation and Restoration

The general techniques of autologous or allogeneic bone marrow transplantation or "rescue" are well known in the art, see for example, F. R. Appelbaum et al., "The Role of Marrow Transplantation in the Treatment of Leukemia", (pp. 229-262), C. D. Bloomfield (ed.), *Chronic and Acute Leukemias in Adults*, Martinus Nijhoff Publishers, Boston (1985); E. D. Thomas, "Clinical Trials with Bone Marrow Transplantation", (pp. 239-253), Clinical Trials in Cancer Medicine, Academic Press, Inc. (1985); E. D. Thomas, *Journal of Clinical Oncology*, 1, 517 (1983); E. D. Thomas et al., *Annals New York Academy of Sciences*, 445, 417 (1985).

Under general or spinal anesthesia and using standard marrow aspiration needles, multiple aspirates are performed from the anterior and posterior iliac crests and, occasionally, the sternum of the donor. The marrow is placed in heparinized tissue culture media and then, using metal screens, filtered to remove bony spicules and fat globules and to create a monocellular suspension. At the time of desired administration of the bone marrow, the marrow is infused intravenously, following which the marrow stem cells migrate to the marrow space, proliferate, and eventually restore normal hematopoiesis and immune function. It is preferable to give as many bone marrow cells as possible to enhance the prospects of marrow engraftment. Following allogeneic transplant the patient usually receives some form of immunosuppression, such as by administration of methotrexate or cyclosporine, in an attempt to prevent or at least modify graft-versus-host disease.

A more preferred method for retrieving bone marrow stem cells involves harvesting these cells from the peripheral blood. The purity of stem cells is enhanced by techniques such as negative selection with antibodies specific for hematopoietic cell markers. In order to increase the concentration of stem cells in the blood, patients are pretreated with chemotherapy, or pretreated with a colony stimulating factor such as G-CSF, GM-CSF, or SC-CSF. These cytokines are also used after TBI and marrow or stem cell transplant to enhance engraftment.

The use of high dose chemotherapy followed by stem cell support has become one of the most attractive therapeutic approaches in multiple myeloma since, in relation to conventional chemotherapy, it increases the number of complete remissions (CR), duration of event free survival (EFS) and probably, overall survival (OS). In this setting of high dose chemotherapy, the use of $^{166}$Ho-DOTMP to suppress (ablate) the marrow in order to eradicate the malignant cells more effectively, requires stem cell support. With total marrow ablation using $^{166}$Ho-DOTMP a stem cell rescue is required using autologous stem cells collected prior to therapy.

Preferably, autologous stem cells or bone marrow cells are purged of cancerous plasma cells or tumor cells by methods known to the art, such as binding the plasma cells with antibody-toxin conjugates or CD34$^-$ selection for stem cell enrichment. The ability to give back the patients stem cells post ablative therapy helps to regenerate the host hematopoiesis and thus protect the patient from potentially life-threatening complications. In the case of multiple myeloma patients treated with the present method, e.g., high dose melphalan and 40-50 Gy of radiation to bone marrow from $^{166}$Ho-DOTMP, the high efficiency of bone marrow suppression effectively increases the negative effect of residual cancer cells in autologous marrow. Therefore, purging autologous cells can improve the outcome for such patients.

Treatment of Cancer

A. Chemotherapeutic Agents

In the treatment of a patient having a cancer such as leukemia or multiple myeloma, the use of the radionuclide compositions described herein can reduce or eliminate the neoplastic cell population in the bone marrow. The aminophosphonate ligands also lead to enhanced uptake of the radionuclide by neoplastic bone lesions, which represent areas of active bone matrix turnover. However, it will usually be necessary to administer one or more chemotherapeutic agents, to destroy the undesirable cells in locations other than the bone marrow or in sanctuaries within the bone marrow, or to add to the effects of the radiation. The efficacy of cancer elimination can be enhanced by the use of protein synthesis inhibitors, in order to inhibit repair of damaged DNA in the cancer cells.

Chemotherapeutic antineoplastic ("anti-cancer") agents that are useful in practicing the present invention include but are not limited to doxorubicin, fludarabine, ifosfamide, thiotepa, melphalan (L-phenylalanine, 4-[bis(2-chloroethyl) amino]-), methotrexate, mitoxantrone, estramustine, bleomycin, vinblastine, taxanes, thalidomide, etoposide, tamoxifen (anti-estrogens) (10-20 mg 2× daily for breast cancer), paclitaxel, vincristine, dexamethasone, busulfan, cyclophosphamide, bischloroethyl nitrosourea, cytosine arabinoside, 6-thioguanine, organoplatinum-based agents and analogs thereof Preferred chemotherapeutic agents that are useful in practicing the present invention, particularly with respect to metastatic breast cancer are doxorubicin, thiotepa, melphalan, methotrexate, bleomycin, vinblastine, taxol, taxanes, tamoxifen, busulfan and analogs thereof. Preferred chemotherapeutic agents, particularly for the treatment of metastatic prostate cancer include mitoxantrone, estramustine, adriamycin and taxanes. Hormone (e.g., anti-androgen) treatment can also be employed to inhibit the spread of prostrate cancer, as can use of non-steroidal aniinflammatory agenst such as etodolac.

Preferred chemotherapeutic agents for treatment of multiple myeloma include melphalan, thalidomide, vincristine, doxorubicin, dexamethosone and doxorubicin.

The present method is particularly advantageous in that it can be used with chemotherapeutic agents, such as alkylating agents, that also suppress bone marrow. For example, melphalan analogs are disclosed in U.S. Pat. Nos. 3,032,584 and 3,032,585 (see Merck Index (11th ed.) at page 914). Conventional dosages and dosage forms of melphalan are disclosed at page 1154 of *Remington's Pharmaceutical Sciences*, Mack Pub. Co. (18th ed. 1990).

The term "chemotherapeutic agent" also includes anticancer agents, such as toxins, that are targeted to cancer cells by antibodies against cancer cell antigens. Such immunoconjugates are described in published PCT applications WO/97/00476 and WO/95/10940. The term chemotherapeutic agent also includes monoclonal antibody based therapies such as herceptin and rituxan (rituximab).

In conjunction with the present method chemotherapy can be given in standard doses; preferably, chemotherapy is given at the upper limit of the conventional ranges or at higher than standard doses, depending on the tolerance of the patient. Standard doses for representative chemotherapeutic agents are shown in the following Table A.

TABLE A

| Chemotherapeutic Agent | Dose* |
|---|---|
| Doxorubicin | 60-120 mg/m$^2$/day |
| Fludarabine | 30-350 mg/m$^2$/day |
| Ifosfamide | 5-10 g/m$^2$ (single dose) |
| Thiotepa | 1.5-500 mg/m$^2$/day |
| Methotrexate | 12-500 mg/m$^2$ i.v. |
| Mitoxantrone | 10-30 mg |
| Estramustine | 50-1120 mg/day |
| Bleomycin | 10-30 U/m$^2$ |
| Vinblastine | 5-10 mg/m$^2$ |
| Docetaxol | 50-200 mg/m$^2$ i.v. |
| Thalidomide | 100-1000 mg/day |
| Paclitaxel | 135-300 mg/m$^2$ |
| Etoposide | 100-5400 mg/m$^2$/day |
| Tamoxifen | 20-60 mg/day |
| Vinorelbine | 20-100 mg/m$^2$/day |
| Vincristine | 1-2 mg/m$^2$/day |
| Dexamethazone | 10-60 mg/day |
| Busulfan | 12-16 mg/kg/day |
| Cyclophosphamide | 750-6000 mg/m$^2$ |
| Carmustine | 250-600 mg/m$^2$ i.v. |
| Cytosine arabinoside | 50-200 mg/m$^2$/day |
| Carboplatin | 100-500 mg/m$^2$/day AUC 4-12 day |

*Ranges from low dose given per day over multiple days to single high daily dose.

B. Adjunct Agents

The mammals (patients) can also be pre-treated with agents such as bisphosphonates, to counteract the hypercalcemia associated with certain tumors, such as lung cancers, multiple myeloma, renal cell carcinoma, bronchogenic carcinoma, breast cancer, lymphoma, and cancers of the head and neck. Pamidronate, clodronate, zaledronate, etidronate, tiludronate and alendronate are preferred agents for treatment of this condition. It will be appreciated that the agents should be selected and used so as not to compete with the therapeutic agent for bone uptake.

The mammals (patients) can be hydrated and premedicated with antiemetics to decrease nausea and vomiting that may be associated with suppression of bone marrow when practicing the present invention. The preferred antiemetics are those that reduce the irritation of the chemoreceptor trigger zone such as Zofran®. Common regimens that are useful in practicing the present invention include serotonin 5-HT$^3$ antagonists such as, for example, ondansteron, granisetron, and the like; dopamine antagonists such as, for example, prochlorperazine, promethazine, droperidol, metoclopramide, and the like; antihistamines and anticholinergics such as, for example, diphenylhydramine, scopolamine, dimethylhydrinate, meclizine, and the like; corticosteroids such as, for example, dexamethasone and the like; and sedatives such as, for example, diazepam, lorazepam, and the like.

C. Cancers Subject to Treatment

A wide variety of leukemias and tumors can be treated with the present complexes including bone-forming or calcific tumors, and fibro-osseous tumors, leukemias such as chronic lymphocytic leukemia and myeloid leukemia, and metastatic tumors to the skeleton. Skeletal system tumors include, but are not limited to, sarcomas such as Ewing's sarcoma, osteochondroma, sarcoma of the periosteum, osteosarcoma, osteoma, osteoblastoma, chondrosarcoma, and giant cell tumor of the bone. Other tumors which can be treated include chordoma, adamanthoma, hemangioendothelioma, hemangiopericytoma, myelomas, such as multiple myeloma, non-Hodgkin's lymphoma, Hodgkin's disease, breast cancer, prostate cancer, lung cancer, head and neck cancer, ovarian cancer, bladder cancer, liver cancer, pancreatic cancer, renal cell carcinoma, myelodysplastic syndrome, germ cell tumor, and neuroblastoma, particularly those cancers that have metastasized to the bone, attach to the bone, or that are associated with the skeletal system. The present method is particularly well-suited for the treatment of various forms and stages of multiple myeloma. Such forms and stages of multiple myeloma are discussed in R. Bataille et al., cited above. Myeloproliferative disorders that are not necessarily classified as cancers, including polycythemia vera, macroglobulinemia, megakaryocytic myelosis or malignant histiocytosis, can also be treated with the present complexes.

D. Adjunct Radiation Therapy

By careful aiming and regulation of dose, high-energy radiation can be used to destroy cancer cells in combination with the present radionuclide therapy. Radiation therapy (also referred to as radiotherapy, x-ray therapy, cobalt treatment, or irradiation) is presently either part of the treatment or the only treatment for about half of all cancer patients. This form of treatment is effective only for those cancer cells within the area receiving the radiation (the field), which can encompass the entirety of the subject's body (total body irradiation or TBI) or can be localized, as in the exposure of a specific tumor site.

Radiation may be used before surgery to shrink a cancerous tumor, after surgery to stop growth of any remaining cancer cells, or alone or with anticancer drugs to destroy a malignant tumor. It is particularly effective when used to treat certain types of localized cancers such as malignant tumors of the lymph nodes or vocal cords.

Radiation usually is not per se curative if the cancer cells have spread throughout the body or outside the area of radiation. It can be used even if a cure is not probable because it can shrink tumors, which decreases the pressure and pain they cause, or it can stop tumor bleeding.

Generally, radiation produces less physical disfigurement than radical surgery, but it may produce severe side effects. These side effects are related to the damage x-rays do to normal tissue such as blood or bone marrow. Side effects include irritated skin, swallowing difficulties, dry mouth, nausea, diarrhea, hair loss, and a loss of energy. How serious and extensive these side effects become depend on where and how much radiation is used.

Use of the present radionuclide complexes can reduce or eliminate the need for total or targeted external radiation therapy, or can enhance the total efficacy of a therapeutic regimen that normally employs TBI. Doses of TBI useful in the present method can deliver total irradiation of from about 750-1350 cGy, e.g., about 800-1000 to 1200 cGy. The total irradiation may be given in multiple fractions, i.e., 1-10 fractions; or in a single dose.

Treatment of Autoimmune Diseases and Immunosuppression

The methods and compositions of the invention are also useful to treat immunologic disorders such as autoimmune diseases by immune suppression due to temporary partial bone marrow suppression or by marrow purging, in combination with marrow transplantation. However, those skilled in the art would recognize that the methods and compositions of the invention can also be used for general immunosuppression in combination with other immunosuppressive therapies. Currently, autoimmune diseases are treated by a variety of nonspecific immunosuppressive drugs and steroids. One group of anti-inflammatory agents used in the treatment of autoimmune diseases is corticosteroids. Corticosteroids are synthetic versions of the body's hormone cortisone, which is produced in small amounts by the adrenal gland. Synthetically produced corticosteroids reduce inflammation and suppress the immune system. The most commonly prescribed corticosteroids for use in treating autoimmune disorders are prednisone and dexamethasone.

Autoimmune disorders are sometimes treated with immunosuppressant drugs such as cytotoxic agents (e.g. methotrexate, azathioprine and cyclophosphamide). In addition, anti-malarials including chloroquine and hydroxychloroquine can be used to suppress inflammation and the immune system in the treatment of autoimmune disorders. Autoimmune diseases can also be treated with nonsteroidal anti-inflammatory medications, such as aspirin, ibuprofen, naproxen, indomethacin, sulindac, etodolac and tolmetin. Gold salts have been used to treat autoimmune arthritis for over a half a century, while recent advances in research have yielded new autoimmune arthritis therapies, such as COX-2 inhibitors. COX-2 inhibitors (or super-aspirin) work to inhibit inflammation and pain without producing significant side effects. In addition, another class of agents that target aberrant cytokine production, such as anti-TNF (tumor necrosis factor) drugs, can also be used for the treatment for several types of autoimmune diseases including rheumatoid arthritis, lupus, myositis, and scleroderma.

Furthermore, the methods and compositions of the invention could also be used alone or in combination with drugs that act more specifically on the immune system, for example, by blocking a particular hypersensitivity reaction. In addition, the complexes could be used in combination with intravenous immunoglobulin therapy or other antibody-based therapies, a treatment, used for various immunological diseases to reduce circulating immune complexes, or specific T cell populations. For example, the present methods and complexes can be used as immunosuppressive agents to inhibit host rejection of transplanted cells, tissue or organs.

In order to increase the chance of the patient's recovery, it can be beneficial to employ hematopoietic cell growth factors, such as granulocyte macrophage colony stimulating factor (GM-CSF), or granulocyte colony stimulating factor (G-CSF), and IL-11 for thrombopoiesis to stimulate or enhance the regeneration and restoration of the bone marrow. It can also be beneficial to employ stem cell growth factor, G-CSF and/or GM-CSF prior to therapy to trigger release of stem cells into the blood where they can be collected.

Infections and Infectious Diseases

The methods and compositions of the invention are also effective to treat bacterial infections, fungal infections, parasitic infections, and infectious diseases that localize to or around bone such as tuberculosis, syphilis, bacterial osteomyelitis, fungal osteomyelitis for example blastomycosis and cryptococcosis, and the like. Anti-fungal agents, and anti-bacterial agents often have poor penetration into the bone and sites enclosed by bone such as the bone marrow. In situations in which the patient is suffering from an infectious disease that has localized to the bone, the patient may be able to achieve a cure by the delivery of high doses of radiation to the bone.

Examples of agents useful in combination with targeted radiation in practicing the present invention include, but are not limited to antibiotic agents, e.g., antibacterial urinary tract agents; anti-infective agents, anti-parasitic agents and anti-fungal agents, including those disclosed in The Physician's Desk Reference, 50th Edition, 1996.

Useful antibiotic agents include systemic antibiotics, such as aminoglycosides, cephalosporins (e.g., first, second, and third generation), macrolides (e.g., erythromycins), monobactams, penicillins, quinolones, sulfonamides, and tetracyclines, including those disclosed in The Physician's Desk Reference, 50th Edition, 1996.

In addition, antibacterial agents include 2-isocephem and oxacephem derivatives disclosed in U.S. Pat. No. 5,919,925; pyridonecarboxylic acid derivatives disclosed in U.S. Pat. No. 5,910,498; water miscible esters of mono- and diglycerides disclosed in U.S. Pat. No. 5,908,862; benzamide derivatives disclosed in U.S. Pat. No. 5,891,890; 3-ammoniopropenyl cephalosporin compounds disclosed in U.S. Pat. No. 5,872,249; 6-O-substituted ketolides disclosed in U.S. Pat. No. 5,866,549; benzopyran phenol derivatives disclosed in U.S. Pat. No. 5,861,430; pyridine derivatives disclosed in U.S. Pat. No. 5,859,032; 2-aminothiazole derivatives disclosed in U.S. Pat. No. 5,856,347; penem ester derivatives disclosed in U.S. Pat. No. 5,830,889; lipodepsipeptides disclosed in U.S. Pat. No. 5,830,855; dibenzimidazole derivatives disclosed in U.S. Pat. No. 5,824,698; alkylenediamine derivatives disclosed in U.S. Pat. No. 5,814,634; organic solvent-soluble mucopolysaccharides disclosed in U.S. Pat. No. 5,783,570; arylhydrazone derivatives disclosed in U.S. Pat. No. 5,760,063; carbapenem compounds disclosed in U.S. Pat. No. 5,756,725; N-acylpiperazine derivatives disclosed in U.S. Pat. No. 5,756,505; peptides disclosed in U.S. Pat. No. 5,714,467; oxathiazines and their oxides disclosed in U.S. Pat. No. 5,712,275; 5-amidomethyl alpha beta-saturated and -unsaturated 3-aryl butyolactone compounds disclosed in U.S. Pat. No. 5,708,169; halogenated benzene derivatives disclosed in U.S. Pat. No. 5,919,438; sulfur-containing heterocyclic compounds disclosed in U.S. Pat. No. 5,888,526; and oral antibacterial agents disclosed in U.S. Pat. No. 5,707,610.

Anti-parasitic agents include agents capable of killing arthropods (e.g., lice and scabies); helminths (e.g., ascaris, enterobius, hookworm, strongloids, trematodes, and trichuris); and protozoa (e.g., amebas, malaria, toxoplasma, and trichomonas), including those disclosed in The Physician's Desk Reference, 50th Edition, 1996.

The methods and compositions of the invention are also effective to treat fungal infections that localize to or around bone such as fungal osteomyelitis and the like. The methods and compositions can also be used in conjunction with antifungal agents known to be useful in the treatment of fungal infections. Antifungal agents include dermatological fungicides, topical fungicides, systemic fungicides, and vaginal fungicides, including those disclosed in The Physician's Desk Reference, 50th Edition, 1996.

In addition, antifungal agents include terpenes, sesquiterpenes diterpenes, and triterpenes disclosed in U.S. Pat. No. 5,917,084; sulfur-containing heterocyclic compounds disclosed in U.S. Pat. No. 5,888,526; carbozamides disclosed in U.S. Pat. No. 5,888,941; phyllosilicates disclosed in U.S. Pat. No. 5,876,738; corynrcandin derivatives disclosed in U.S. Pat. No. 5,863,773; sordaridin derivatives disclosed in U.S. Pat. No. 5,854,280; cyclohexapeptides disclosed in U.S. Pat. No. 5,854,213; terpene compounds disclosed in U.S. Pat. No. 5,849,956; agents derived from aspergillus fumigatus disclosed in U.S. Pat. No. 5,873,726; inula extracts disclosed in U.S. Pat. No. 5,837,253; lipodepsipeptides disclosed in U.S. Pat. No. 5,830,855; polypeptides disclosed in U.S. Pat. No. 5,824,874; pyrimidone derivatives disclosed in U.S. Pat. No. 5,807,854; agents from sporomiella minimizes disclosed in U.S. Pat. No. 5,801,172; cyclic peptides disclosed in U.S. Pat. No. 5,786,325; polypeptides disclosed in U.S. Pat. No. 5,773,696; triazoles disclosed in U.S. Pat. No. 5,773,443; fusacandins disclosed in U.S. Pat. No. 5,773,421; terbenzimidazoles disclosed in U.S. Pat. No. 5,770,617; and agents obtained from hormones disclosed in U.S. Pat. No. 5,756,472.

Pathologies Treatable by BMT or Stem Cell Replacement

The present methods can be useful to ablate bone marrow in treatment regimens intended to correct a variety of disorders by replacing "defective" hematopoietic cells, with "normal" autologous or allogeneic bone marrow or stem cells. This can be used in the treatment of diseases of red cells and bleeding disorders. These include hematopoietic genetic diseases such as hemolytic anemias, i.e., sickle cell anemia or thalassemia. Other such disorders include various anemias, polycythemia, thrombocytopenia, and bleeding disorders related to defective platelet function or abnormalities in clotting factors.

Hematopoietic stem cell transplantation from normal donor has been reported to be effective to treat lysosomal and peroxisomal storage diseases, such as globoid cell leukodystrophy, metachromatic leukodystrophy, adrenoleukodystrophy, mannosidosis, flucosidosis, aspartylglucosaminuria; Harder, Maroteaux-Lamy and Sly Syndromes and Gaucher disease type III. W. Krivit et al., *Curr. Opin. Neurol.*, 12, 167 (1999).

Gene Therapy

The present method can also be employed as part of gene therapy that involves implantation of genetically engineered stem cells, to correct genetic defects, following bone marrow ablation. For example, a subject's own stem cells can be "normalized" by introduction of a vector comprising a gene that will effectively counteract the defective gene or replace the missing one. See, D. B. Kohn, *Curr. Opinion in Pediatr.*, 7, 56 (1995).

Bone marrow suppression, followed by administration of genetically engineered (transformed) stem cells, can be used, for example, in the treatment of cancer in a human by inserting exogenous genes into human primary cells, such as, for example, stem cells, which specifically "target" mature blood cells to a tumor. Preferably, the stem cells have been removed from a cancer patient and expanded in culture. Genes that enhance the anti-tumor effects of the mature cells can also be employed. The blood cells can be expanded in number before or after insertion of the genes. A method for transforming blood cells is described in U.S. Pat. No. 5,286,497. Thus, the procedure is performed in such a manner that upon injection into the patient, the transformed blood cells will produce an anti-cancer agent in the patient's body, preferably at the site of the tumor itself.

The gene carried by the transformed stem cells can be any gene that directly or indirectly enhances the therapeutic effects of the resultant mature blood cells such as a recombinant normal human gene. The gene carried by the stem cells can be any gene that allows the blood cells to exert a therapeutic effect that it would not ordinarily have, such as a gene encoding a clotting factor useful in the treatment of hemophilia. Examples of other suitable genes include those that encode cytokines such as TNF, interleukins (interleukins 1-12), interferons ($\alpha$, $\beta$, $\gamma$-interferons), T-cell receptor proteins and Fc receptors for antigen-binding domains of antibodies, such as immunoglobulins.

Additional examples of suitable genes include genes that modify blood cells to "target" to a site in the body to which the blood cells would not ordinarily "target," thereby making possible the use of the blood cell's therapeutic properties at that site. In this fashion, blood cells can be modified, for example, by introducing a Fab portion of a monoclonal antibody into the stem cells, thereby enabling the mature blood cells to recognize a chosen antigen. Other genes useful in cancer therapy can be used to encode chemotactic factors that cause an inflammatory response at a specific site, thereby having a therapeutic effect. Other examples of suitable genes include genes encoding soluble CD4 which is used in the treatment of AIDS and genes encoding preselected polypeptides or protein that can act to correct or ameliorate genetic disorders which result in insufficient or defective enzymes. Such genes include the α-antitrypsin gene, which is useful in the treatment of emphysema caused by α-antitrypsin deficiency, a tyrosine hydroxylase gene (Parkinson's disease), a glucocerebrosidase gene (Gaucher's disease), an α-galactosidase gene (Fabray's disease) an arylsulfatase A gene (metachromatic leukodystrophies), an insulin gene for use in diabetes, or genes encoding other polypeptides or proteins.

The gene therapy of the present invention is also useful in the treatment of a variety of diseases including but not limited to adenosine deaminase deficiency, sickle cell anemia, thalassemia, hemophilia, diabetes, α-antitrypsin deficiency, brain disorders such as Alzheimer's disease, and other illnesses such as growth disorders and heart diseases, for example, those caused by alterations in the way cholesterol is metabolized and defects of the immune system.

One of skill in the art would recognize that the conditions discussed herein above can have multiple causes and can overlap in naming and categorization.

The following examples are included to aid in the understanding of the invention but are not to be construed as limiting the invention.

EXAMPLE 1

$^{166}$Ho-DOTMP Preparation

Ho-165-nitrate targets are prepared from dissolution of holmium oxide in nitric acid followed by reduction to dryness. A target containing 6 mg of holmium is irradiated in a reactor for approximately 155 hours at a flux of $4.5 \times 10^{14}$ n/cm$^2$/s. The specific activity is typically in the range of 1.3-2 Ci/mg.

The $^{166}$Ho-nitrate target is dissolved in 0.3 N HCl. In a typical 9 Ci preparation, $^{166}$Ho-chloride is supplied in 10 ml of 0.3 N HCl. Six vials of DOTMP (each vial containing 10 mg DOTMP and 28 mg NaOH) is dissolved in 4 ml water and added to the $^{166}$Ho chloride. The ligand to metal ratio is 3.5. The reaction mixture is allowed to mix for 10 minutes at a pH of 10.5. This is followed by addition of 4.8 ml of 1.0 M sodium phosphate buffer and ascorbic acid. The final concentration of ascorbic acid is 55 mg/ml. Dilution with water may be performed to assure that the final activity concentration does not exceed 322 mCi/ml. The pH of the final product is 7-8.

EXAMPLE 2

Preparation of $^{153}$Sm-Solution

Sm-153 is produced by irradiating 99.06 percent enriched $^{152}$Sm$_2$O$_3$ in the first row reflector at a neutron flux of $8 \times 10^{13}$ neutron/cm$^2$×sec, or at high flux of $4.5 \times 10^{14}$ n/cm$^2$/sec, at the Missouri University Research Reactor (MURR). Irradiations are generally carried out for 50 to 60 hours, yielding a Sm-153 specific activity of 1000-1300 Ci/g.

To irradiate Sm$_2$O$_3$ for production of Sm-153, the desired amount of target is first weighed into a quartz vial, the vial flame sealed under vacuum and welded into an aluminum can. The can is irradiated for the desired length of time, cooled for several hours and opened remotely in a hot cell. The quartz vial is removed and transferred to a glove box, opened into a glass vial that is then sealed. An appropriate amount of a solution of hydrochloric acid is then added to the vial via syringe in order to dissolve the Sm$_2$O$_3$. Once the Sm$_2$O$_3$ is dissolved, the samarium solution is diluted to the appropriate volume by addition of water. The solution is removed from the original dissolution vial that contains the shards of the quartz irradiation vial, and transferred via syringe to a clean glass serum vial.

EXAMPLE 3

Preparation of $^{159}$Gd Solution

Gadolinium-159 is prepared by sealing gadolinium oxide (1.1 mg) into a quartz vial. The vial is welded inside an aluminum can and irradiated for 30 hours in a reactor at a neutron flux of $8 \times 10^{13}$ neutron/cm$^2$×sec. The contents of the quartz vial are dissolved using HCl. Water is added to obtain a solution of Gd-159 in 0.1N HCl.

EXAMPLE 4

Preparation of $^{153}$Sm-DOTMP

The DOTMP ligand (22 mg) was dissolved in 878 μL of distilled water and 15 μL of 50% NaOH. A volume of 15 μL of this solution was transferred to a vial containing 1.5 mL of Sm solution (0.3 mM Sm in 0.1N HCl spiked with 2 μL of Sm-153 tracer). The pH was adjusted to 7-8 using NaOH and the amount of Sm found as a complex was greater than 99% as determined by ion exchange chromatography. This yielded a solution containing Sm at 0.3 mM with a ligand to metal molar ratio of approximately 1.5.

EXAMPLE 5

Preparation of $^{166}$Ho-DOTMP

The DOTMP ligand (22 mg) was dissolved in 878 μL of distilled water and 15 μL of 50% NaOH. A volume of 30 μL of this solution was transferred to a vial containing 1.5 ml of Ho solution (0.6 mM Ho in 0.1N HCl spiked with 2 μL of $^{166}$Ho tracer). The pH was adjusted to 7-8 using NaOH and the amount of Ho found as a complex was greater than 99% as determined by ion exchange chromatography. This yielded a solution containing 0.6 mM Ho with a ligand to metal molar ratio of approximately 1.5.

EXAMPLE 6

Pharmacokinetics and Patient Specific Dosimetry of High Dose $^{166}$Ho-DOTMP Therapy Used for Treatment of Breast Cancer Metastatic to Bone Eight patients with breast cancer metastatic only to bone initially received a 30 mCi dose of $^{166}$Ho-DOTMP for diagnostic purposes. Pharmacokinetics were assessed via whole body counting, gamma camera imaging, and urine and blood assays for the first 48 hours following injection. Patients were followed with autologous stem cell transplantation for rescue from hematologic toxicity.

The average percentage uptake in the skeleton was 28±12% (range: 15% to 47%), with an effective skeletal half-life of 19.9±2.5 hours (range: 15 to 23 hours). Approximately 50% of the material was present in the urine at 6 hours post injection. Whole blood clearance was rapid and biphasic: early $T_{1/2}$: 0.05±0.04 hours: late $T_{1/2}$: 11±4 hours with, on average, a small percentage of the injected dose remaining at 24 hours post injection.

Therapy doses were calculated based upon prescribed dose to the red bone marrow using the Medical Internal Radiation Dose (MIRD) technique and percentage localization in the skeleton. Appropriate S-values were provided by Oak Ridge National Laboratory. The desired target dose was 22 Gy to the red marrow calculated by the above technique for each individual. The average red marrow dose was calculated to be 1.97±0.92 cGy/mCi (range: 0.98 cGy/mCi to 3.19 cGy/mCi). Three patients proceeded to therapy, two were disqualified due to low uptake in the skeleton (<30%; revised qualification: 15%), and three were disqualified for other reasons unrelated to the $^{166}$Ho-DOTMP treatment. Other than severe hematological suppression, no toxicity was noted.

EXAMPLE 7

$^{166}$Ho-DOTMP-Melphalan Treatment of Multiple Myeloma (MM) Patients

Multiple myeloma patients(≦65 yrs. of age) that have responded to initial chemotherapy or have primary refractory disease or chemotherapy responsive relapse, but who are not in refractory relapse are treated. Patients are well hydrated with fluids during the day prior to the diagnostic dose. An initial diagnostic dose of 30 mCi of $^{166}$Ho-DOTMP is administered to confirm the selective localization to the skeleton, establish the in-vivo pharmacokinetics and provide radiation dosimetry estimates for the red marrow. Assuming >15% of the $^{166}$Ho-DOTMP accumulates in bone following the injection, the amount of $^{166}$Ho-DOTMP required for therapy is calculated based on delivering a specified radiation absorbed dose to the marrow. Patients receive the therapeutic dose by intravenous injection over 5-10 minutes, given over 1-3 days ≧48 hrs after the dosometry (test) dose.

The time line for conducting the investigation is as follows: Test dose $^{166}$Ho-DOTMP (30 mCi); $^{166}$Ho scan image (0, 4-6, 20-24 hr.); Blood samples for dosimetry (10, 30 min, 1, 2, 6, 20-24 hr.); Urine samples (0-6, 6-12, 12-24, 24-48 hr.); and External whole body probe (0, 2, 6, 24 and 48 hr.).

Melphalan is administered 48 hr prior to the predicted PBSC infusion based upon dosimetry assessment from the test dose. PBSC infusion is administered when bone marrow dose from $^{166}$Ho is ≦1 cGy/hr. Patients were treated at 20, 30, 40 and prospectively 50 Gy, and with 140 mg/m$^2$ and 200 mg/m$^2$ melphalan. The results are shown in Table 2, hereinbelow.

The MTD was defined as the level that is associated with a true toxicity rate of 20%, where toxicity for these purposes was taken to be grade 3 or greater extramedullary drug related toxicity.

All toxicities encountered during the study will be evaluated according to Bearman criteria (Bearman et al., *J Clin Oncol*, 6, 1562, (1988)). Graft failure is considered a grade 3 toxicity. Graft failure is defined as failure to recover granulocytes to 0.5×10$^9$/l or platelets 20×10$^9$/l within 28 days of transplant or a fall to less than these levels for 3 or more consecutive days after day 28 without other apparent cause. Hematopoietic recovery (engraftment) is defined as having a sustained granulocyte count of 0.5×10$^9$/l for two consecutive counts post transplant and a platelet count 20×10$^9$/l for seven consecutive counts post transplant, without transfusion support. The first of two counts for the granulocyte count and the first of seven counts for the platelet count are considered the day of engraftment.

Patients undergo blood stem cell infusion at the time when ongoing radiation to the marrow falls to <1 rad/hr, and at least 24 hours after melphalan infusion. The total volume of stored cells is infused into a free flowing IV line primed with normal saline. Patients are premedicated with acetaminophen 650 mg PO and diphenhydramine 50 mg PO or IV. All patients receive conventional supportive care for autologous/syngeneic blood and marrow transplantation, (such as allopurinol, menstrual suppression, prophylactic antibiotics, empiric antibiotics, IV Ig, transfusions of blood products, hyperalimentation, and the like).

EXAMPLE 8

Single Dose $^{166}$Ho-DOTMP Treatment with Melphalan

Well hydrated mammals (Humans should be instructed to take in fluids in excess of 2000 cc during the prior 24 hours.) are administered an initial diagnostic dose of 30 mCi to confirm the selective localization to the skeleton, establish the in-vivo pharmacokinetics, skeletal uptake, and provide radiation dosimetry estimates for the red marrow. The actual dosage is of the $^{166}$Ho required for therapy will be calculated on the basis of percent uptake in the skeleton and that value used to deliver the specified radiation absorbed dose to the marrow. Patients will receive the therapeutic dose of 20 Gy (370-1110 megabecquerels per kilogram of body weight) or 30 Gy (555-1665 megabecquerels per kilogram of body weight) or 40 Gy (740-2220 megabecquerels per kilogram of body weight) or 50 Gy (925-2775 megabecquerels per kilogram of body weight) by intravenous injection over 2-10 minutes given on a single day. The mammals are then administered melphalan, 140 mg/m$^2$, 200 mg/m$^2$ or 220 mg/m$^2$, 48 hours prior to stem cell (PBSC) infusion which occurs about 6-8 days after $^{166}$Ho-DOTMP administration, when the bone marrow exposure rate drops below 1 cGy/hour. Mammals are started on granulocyte-colony stimulating factor (G-CSF) at a dose of 5-10 mcg/kg/day, and continued until the granulocyte count is 1×10$^9$/L for 3 consecutive days. Mammals are also administered prophylactic antibiotic and antifungal agents while neutropenic.

EXAMPLE 9

Single Dose $^{166}$Ho-DOTMP Treatment with Melphalan and TBI

Well hydrated mammals (Humans should be instructed to take in fluids in excess of 2000 cc during the prior 24 hours.) are administered an initial diagnostic dose of 30 mCi to confirm the selective localization to the skeleton, establish the in-vivo pharmacokinetics, skeletal uptake, and provide radiation dosimetry estimates for the red marrow. The actual dosage is of the $^{166}$Ho required for therapy will be calculated on the basis of percent uptake in the skeleton and that value used to deliver the specified radiation absorbed dose to the marrow. Patients will receive the therapeutic dose of 20 Gy (370-1110 megabecquerels per kilogram of body weight) or 30 Gy (555-1665 megabecquerels per kilogram of body weight) or 40 Gy (740-2220 megabecquerels per kilogram of body weight) or 50 Gy (925-2775 megabecquerels per kilogram of body weight) by intravenous injection over 2-10 minutes given on a single day. This is then followed by TBI (800 cGy in four fractions) on successive days. The mammals are then administered melphalan, 140 mg/m$^2$, 48 hours prior to peripheral blood stem cell (PBSC) infusion which occurs about 6-8 days after $^{166}$Ho-DOTMP administration, when the bone marrow exposure rate drops below 1 cGy/hour. Mammals are started on granulocyte-colony stimulating factor (G-CSF) at a dose of 5-10 mcg/kg/day, and continued until the granulocyte count is 1×10$^9$/L for 3 consecutive days. Mammals are also administered prophylactic antibiotic and antifungal agents while neutropenic.

EXAMPLE 10

$^{166}$Ho-DOTMP Treatment

Well hydrated mammals (Humans should be instructed to take in fluids in excess of 2000 cc during the prior 24 hours.) are administered an initial diagnostic dose of 30 mCi to confirm the selective localization to the skeleton, establish the in-vivo pharmacokinetics, skeletal uptake, and provide radiation dosimetry estimates for the red marrow. The actual dosage of the $^{166}$Ho required for therapy will be calculated on the basis of percent uptake in the skeleton and that value used to deliver the specified radiation absorbed dose to the marrow. Patients will receive the therapeutic dose of 50 Gy (2000-3000 megabecquerels per kilogram of body weight) by intravenous injection over 2-10 minutes given on a single day. When the bone marrow exposure rate drops below 1 cGy/hour mammals are started on granulocyte-colony stimulating factor (G-CSF) at a dose of 5-10 mcg/kg/day, and continued until the granulocyte count is 1×10$^9$/L for 3 consecutive days. Mammals are also administered prophylactic antibiotic and antifungal agents while neutropenic.

EXAMPLE 11

Following the procedures described in Examples 7-9, patients, afflicted with multiple myeloma, were treated according to the method of the present invention. The results are described in table 2, below. These results demonstrate that the combination of 200 mg/m$^2$ melphalan and Ho-DOTMP is at least as efficatious or is more efficatious than the combination of 140 mg/m$^2$ melphalan with Ho-DOTMP, either with or without TBI. Additionally, the combination of 200 mg/m$^2$ melphalan and Ho-DOTMP did not produce more grade 3 toxicity than the other therapies.

The three protocols enrolling patients using $^{166}$Ho for multiple myeloma have accrued 72 patients, with 66 evaluable for safety and 40 evaluable for response. The original protocol treating patients with melphalan (140 mg/m$^2$) without TBI was amended to increase the dose of melphalan to 200 mg/m$^2$. The increase in melphalan was to determine if $^{166}$Ho-DOTMP could be given in combination with high dose melphalan without added unmanageable toxicity.

The melphalan (140 mg/m$^2$)/TBI/$^{166}$Ho-DOTMP protocol has treated 24 patients total, 17 of which were evaluable.

The melphalan (140 mg/m$^2$)/$^{166}$Ho-DOTMP protocol has treated 16 patients, 14 of which were evaluable.

The melphalan (200 mg/m$^2$)/$^{166}$Ho-DOTMP protocol has treated 32 patients, 9 of which were evaluable.

The dosage range of radiation from the complex was 460 mCi to 4.5 Ci.

To date there have been no major, unexpected extramedullary toxicities related to therapy>grade 2. One patient had graft failure and one had delayed platelet engraftment on the TBI protocol and as a result 4 additional patients were enrolled at that dose level. Of those additional patients, no further graft toxicities were observed. There were five patient deaths but none attributable to the study drug.

The primary toxicity in all patients treated to date has been mucositis. This toxicity has been well managed in all patients, and no patients have experienced any mucositis>grade 2. The addition of targeted radiotherapy has not resulted in any increased toxicity beyond what would be expected in the standard treatment population. Representative case studies are described in Examples 12-14, below.

In order to achieve a complete response using protocol criteria, a patient must have a complete absence of any myeloma protein in the blood/urine and marrow post treatment. The patient must have normal bone marrow with complete resolution of plasmocytomas and no increase in bone lesions. To meet international standards, this must be maintained for 6 weeks. While response rates to a conventional high dose therapy vary widely, in general for previously treated patients, there is a range of 5-25% CR rate.

Partial response is defined as sustained decrease in the production rate of the monoclonal serum protein to 25% or less of the pretreatment value for at least 2 months. Calculations consider the serum myeloma protein concentration, variations in catabolic rate with changing concentration, and changes in estimated plasma volume. Response requires a

TABLE 2

|  | 140 mg/m$^2$ melphalan w/o TBI | | | 140 mg/m$^2$ melphalan w/TBI | | | 200 mg/m$^2$ melphalan w/o TBI | | |
| --- | --- | --- | --- | --- | --- | --- | --- | --- | --- |
| Ho-DOTMP Dose to Marrow: | 20 Gy | 30 Gy | 40 Gy | 20 Gy | 30 Gy | 40 Gy | 20 Gy | 30 Gy | 40 Gy |
| Days to ANC >500 | 10 | 16 | 12 | 9 | 11 | 9 | 10 | 12 | 10.5 |
|  | (8-13) | (13-17) | (9-13) | (9-16) | (9-14) | (9-10) | (10-10) | (9-19) | (9-13) |
| Days to Platelets >20,000 | 10 | 10 | 10 | 12 | 12 | 13 | 11 | 10 | 10 |
|  | (7-14) | (7-44) | (7-19) | (9-19) | (7-28) | (8-21) | (9-19) | (6-10) | (7-15) |
| Number of Patients w/Grade 3 Toxicity | 0/5 | 0/4 | 0/7 | 0/8 | 1/8 | 0/20 | 0/4 | 0/7 | 0/14 |
| Complete Response |  | 3/4 |  |  | 7/17 |  |  | 8/9 |  |

ANC = Absolute neutrophil count
NA = Not Available sustained 24 hour urine Bence Jones protein excretion to less than 0.1 gm/day for at least 2 measurements.

Based on the 40 patients that have response data and have been monitored, currently there is a 45% complete response rate, with an overall response rate (CR and PR) of 55% on these protocols.

EXAMPLE 12

Treatment: 20 Gy $^{166}$Ho-DOTMP, Melphalan 140 mg/m$^2$

The patient, a 47 year-old male with an original diagnosis of multiple myeloma, was administered a therapeutic dose of $^{166}$Ho-DOTMP of 3875 mCi which was calculated to deliver 40 Gy to the marrow. Post $^{166}$Ho-DOTMP, the patient received a dose of 140 mg/m$^2$ of melphalan (I.V.). The patients stem cells were reinfused three days after the melphalan and were followed by G-CSF for ten days.

Nine days post stem cell transplant, the patient engrafted neutrophils (ANC >500), and fourteen days post transplant, the patient engrafted platelets (>20,000). Twenty-eight days post transplant the patient was in complete remission.

EXAMPLE 13

Treatment: 20 Gy $^{166}$Ho-DOTMP, Melphalan 140 mg/m$^2$ + 800 cGy Total Body Irradiation The patient, a 54 year-old male with an original diagnosis of free kappa light chain multiple myeloma and currently with primary refractory disease, was administered 29.1 mCi (61.4 cGy of $^{166}$Ho-DOTMP as a diagnostic dose. Based on dosimetry, a therapeutic dose of 1660 mCi (61.46 GBq) was calculated to deliver 20 Gy to the marrow. The actual therapeutic dose injected was 1555 mCi. Three days post $^{166}$Ho-DOTMP the patient received a dose of 140 mg/m$^2$ of Melphalan (I.V.) for a total dose of 269 mg. One day post Melphalan the patient received the first of four days of total body irradiation (TBI). The total dose of TBI was 800 cGy fractionated into four doses of 200 cGy. The patient's stem cells were reinfused after the last dose of TBI and were followed by G-CSF at a total dose of 480 mcg for ten days.

Ten days post stem cell transplant the patient engrafted neutrophils (absolute neutrophil count (ANC) >500), and nine days post transplant the patient engrafted platelets (>20,000). One month post treatment the patient was determined to have a complete remission.

EXAMPLE 14

Treatment: 20 Gy $^{166}$Ho-DOTMP, Melphalan 140 mg/m$^2$

The patient, a 59 year-old female with an original diagnosis of multiple myeloma and currently diagnosed with primary refractory disease, was premedicated with an antiemetic, IV Zofran at 8 mg Q8h, this was continued post injection for three days.

The patient was administered 29.4 mCi of $^{166}$Ho-DOTMP as a diagnostic dose, based on dosimetry a therapeutic dose of 582 mCi was calculated to deliver 20 Gy to the marrow. The actual therapeutic dose injected was 460 mCi. Six days post $^{166}$Ho-DOTMP the patient received a dose of 140 mg/m$^2$ of Melphalan (I.V.) for a total dose of 220 mg. The patient's stem cells were reinfused three days after the Melphalan and were followed by G-CSF at a total dose of 300 mcg for ten days.

Ten days post stem cell transplant the patient engrafted neutrophils (absolute neutrophil count (ANC) >500), and fourteen days post transplant the patient engrafted platelets (>20,000). Five months post treatment the patient was determined to have a complete remission.

EXAMPLE 15

Stability of Metal Ligand Complexes with Stabilizer:

Samples of $^{166}$Ho-DOTMP were prepared according to the procedure in Example 1 using ascorbic acid, 55 mg/mL, as the stabilizer. Identical samples were prepared without ascorbic acid. The solutions were analyzed for radiochemical purity after 1 hour, 6 hours, 10 hours, 24 hours, and 48 hours, using Instant Thin Layer Chromatography (ILTC), Cation Exchange Chromatography (CEC) and High Performance Liquid Chromatography (HPLC). As can be seen in the Table 3, the use of a radioprotectant (stabilizer) allowed the sample to maintain high radiochemical purity over samples without any stabilizer.

TABLE 3

| | Time (hrs) | | | | |
|---|---|---|---|---|---|
| | 1 | 6 | 10 | 24 | 48 |
| ITLC | | | | | |
| Without stabilizer | 99.2 | 98.1 | 97.5 | 97.6 | 96.5 |
| With stabilizer | 99.0 | 99.2 | 99.6 | 99.6 | 99.6 |
| CEC | | | | | |
| Without stabilizer | 99.0 | 97.8 | 97.8 | 97.2 | 97.1 |
| With stabilizer | 98.4 | 99.0 | 99.6 | 98.5 | 98.7 |
| HPLC | | | | | |
| Without stabilizer | 100 | 95.4 | 94.9 | 85.8 | |
| With stabilizer | 100 | 100 | 99.0 | 98.7 | |

EXAMPLE 16

Biodistribution Study of $^{166}$Ho-DOTMP in Rats

Sprague Dawley (S. D.) rats were injected intravenously (inj. i.v.) with a solution of $^{166}$Ho-DOTMP ("Ho-DO") containing ascorbic acid (asc) as a stabilizer. The animals were sacrificed and organs excised and counted in a radioactive well counter after decay to appropriate levels. Bone (femur) samples were counted and converted to a total bone percent injected dose using a factor of 25 times femur percent.

A second group of Sprague Dawley rats were injected intravenously with a solution of $^{166}$Ho-DOTMP without having the stabilizer. The animals were sacrificed and organs excised and counted in a radioactive well counter after decay to appropriate levels. Bone (femur) samples were counted and converted to a total bone percent injected dose using a factor of 25 times femur percent.

The results of this study show that the addition of the stabilizing agent, ascorbic acid, lowered the uptake of radiation by the non-target organs, while equivalent bone uptake was seen. In both control and stabilized preparations, high uptake and specificity for skeletal targeting was shown.

Figure 2:
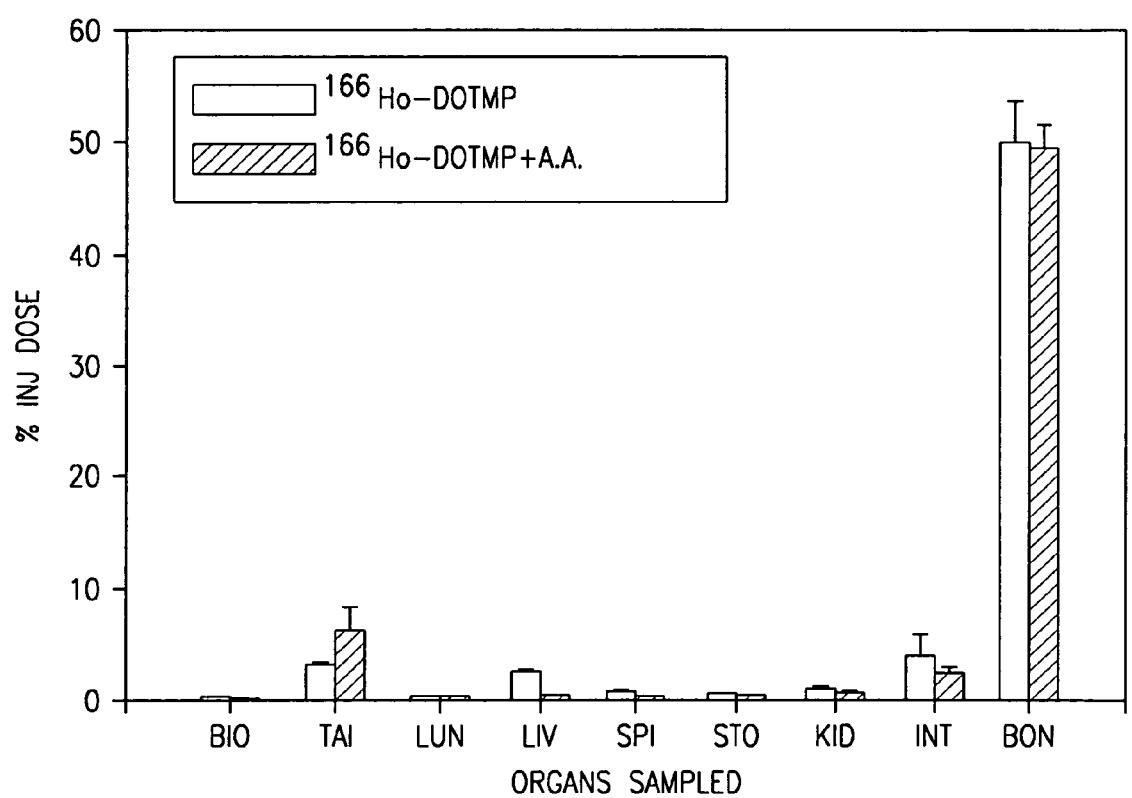
FIGS. 2-4 are graphical representations of a comparison of the uptake of $^{166}$Ho-DOTMP in bones and non-target organs when using a stabilizer.
Figure 3:
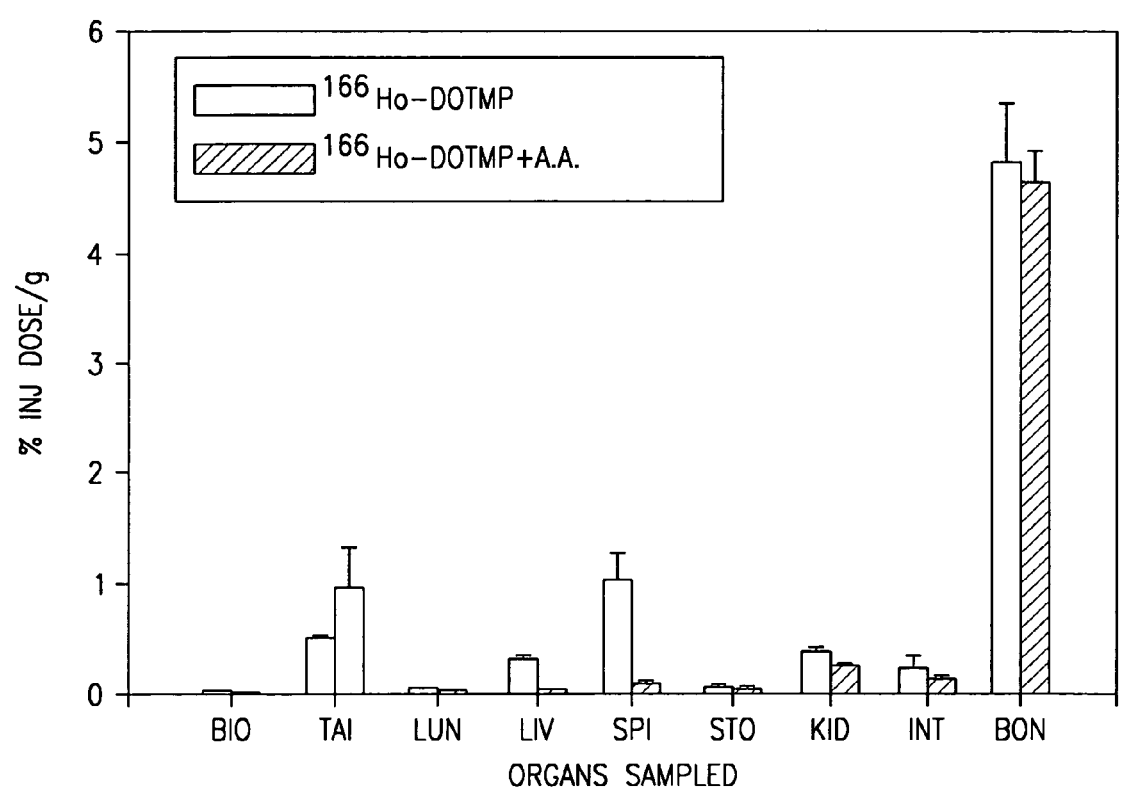
Figure 4:
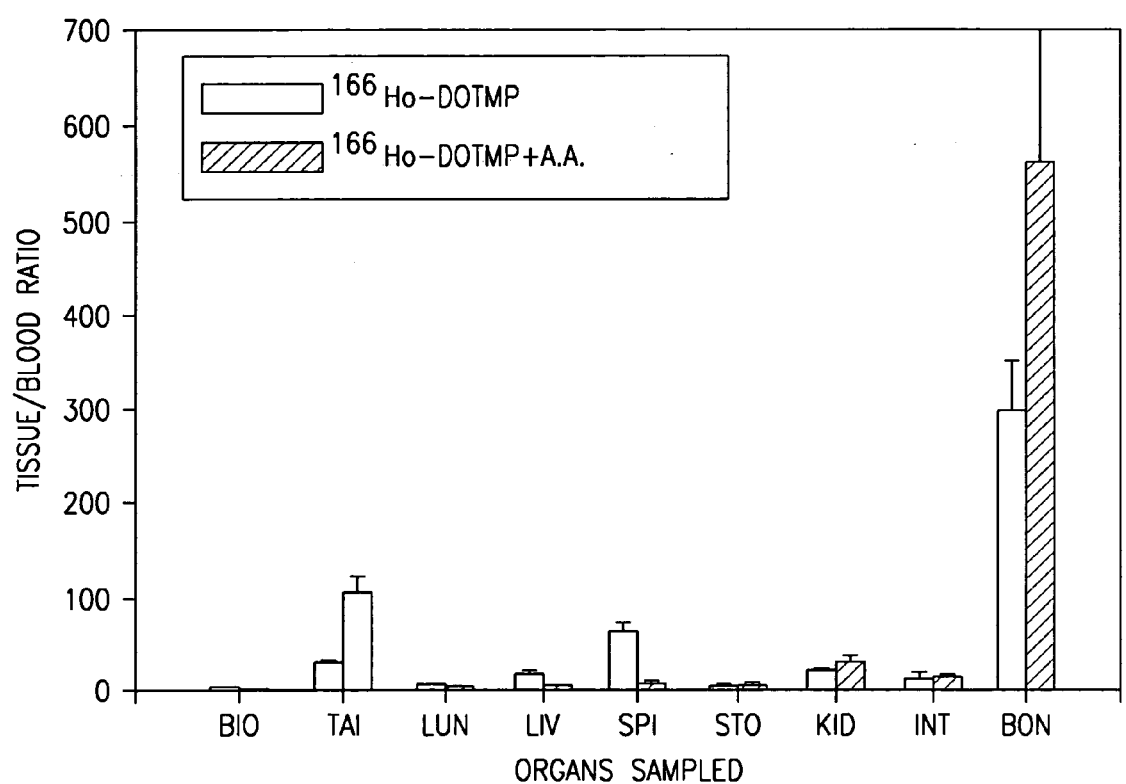

Results are illustrated summarized in Tables 4-6 and in FIGS. 2-4. FIG. 2 illustrates the data uptake base on the % injection dose. FIG. 3 illustrates the data uptake base on the % injection dose per gram(mass). FIG. 4 illustrates the data uptake base on the tissue/blood ratio. Abbreviations: Blo=blood; Tai=tail; Lun=lung; Liv=liver; Spl=spleen; Sto=stomach; Kid=kidneys; Int=intestines; Bon=bone; SD=standard deviation.

TABLE 4

Percent Injection Dose/Gram

|  | Ho-DO only | SD | Ho-DO + asc | SD |
|---|---|---|---|---|
| Blood | 0.02 | 0.00 | 0.01 | 0.00 |
| Tail | 0.51 | 0.02 | 0.95 | 0.36 |
| Lung | 0.04 | 0.01 | 0.03 | 0.00 |
| Liver | 0.31 | 0.03 | 0.03 | 0.01 |
| Spleen | 1.03 | 0.24 | 0.08 | 0.02 |
| Stomach | 0.05 | 0.03 | 0.04 | 0.03 |
| Kidney | 0.38 | 0.04 | 0.25 | 0.02 |
| Intestine | 0.23 | 0.11 | 0.13 | 0.03 |
| Bone | 4.84 | 0.52 | 4.65 | 0.29 |

TABLE 5

Percent Injection Dose

|  | Ho-DO only | SD | Ho-DO + asc | SD |
|---|---|---|---|---|
| Blood | 0.29 | 0.04 | 0.16 | 0.03 |
| Tail | 3.21 | 0.14 | 6.19 | 2.11 |
| Lung | 0.00 | 0.00 | 0.00 | 0.00 |
| Liver | 2.40 | 0.23 | 0.24 | 0.05 |
| Spleen | 0.56 | 0.11 | 0.04 | 0.01 |
| Stomach | 0.20 | 0.13 | 0.21 | 0.17 |
| Kidney | 0.72 | 0.07 | 0.47 | 0.03 |
| Intestine | 3.81 | 1.88 | 2.23 | 0.56 |
| Bone | 50.05 | 3.85 | 49.58 | 2.12 |

TABLE 6

Tissue/Blood Ratio

|  | Ho-DO only | SD | Ho-DO + asc | SD |
|---|---|---|---|---|
| Blood | 1.00 | 0.00 | 1.00 | 0.00 |
| Tail | 31.33 | 3.84 | 104.71 | 16.20 |
| Lung | 2.34 | 0.45 | 3.01 | 0.50 |
| Liver | 18.90 | 2.11 | 3.40 | 0.97 |
| Spleen | 62.09 | 12.64 | 8.53 | 1.85 |
| Stomach | 3.24 | 2.04 | 5.01 | 4.44 |
| Kidney | 22.84 | 1.33 | 30.69 | 8.12 |
| Intestine | 13.80 | 7.66 | 14.60 | 2.73 |
| Bone | 296.80 | 52.34 | 563.40 | 137.47 |

EXAMPLE 17

Treatment of breast cancer will be in conjunction with high-dose combination chemotherapy regimens such as CTCb (STAMP V): Cyclophosphamide 1500 mg/m$^2$, Thiotepa 125 mg/m$^2$, Carboplatin 200 mg/m$^2$ administered intravenously over one or several days. Chemotherapeutics will preferably be administered following the Ho-DOTMP but may be given prior to or simultaneously.

EXAMPLE 18

Breast cancer, particularly metastatic breast cancer, will be treated with the present complexes, e.g., with $^{166}$Ho-DOTMP in accord with the present method, employing the regimens listed on Table 7.

TABLE 7

Breast Cancer Regimens

| Regimens | Chemotherapeutic Agent(s) |
|---|---|
| | Combination Regimens |
| AC | Doxorubicin 40-45 mg/m$^2$ i.v., day 1<br>WITH<br>Cyclophosphamide 200 mg/m$^2$ PO, days 3-6<br>Repeat cycle every 21 days<br>OR<br>Cyclophosphamide 500 mg/m$^2$ i.v., day 1<br>Repeat cycle every 28 days |
| CAF(FAC) | Cyclophosphamide 600 mg/m$^2$ i.v., day 1<br>Doxorubicin 60 mg/m$^2$ i.v., day 1<br>Fluorouracil 600 mg/m$^2$ i.v., days 1, 8<br>Repeat cycle every 28 days<br>OR<br>Cyclophosphamide 500 mg/m$^2$ i.v., day 1<br>Doxorubicin 50 mg/m$^2$ i.v., day 1<br>Fluorouracil 500 mg/m$^2$ i.v., days 1<br>Repeat cycle every 21 days and day 8 (FAC) |
| CFM (CNF, FNC) | Cyclophosphamide 600 mg/m$^2$ i.v., day 1<br>Fluorouracil 600 mg/m$^2$ i.v., day 1<br>Mitoxentrone 12 mg/m$^2$ i.v., day 1<br>Repeat cycle every 21 days |
| CMF | Cyclophosphamide 100 mg/m$^2$ PO, days 1-14<br>or 600 mg/m$^2$ i.v., days 1, 8<br>Methotrexate 40 mg/m$^2$ i.v., days 1, 8<br>Fluorouracil 600 mg/m$^2$ i.v., days 1, 8<br>Repeat cycle every 28 days<br>OR<br>Cyclophosphamide 600 mg/m$^2$ i.v., day 1<br>Methotrexate 40 mg/m$^2$ i.v., day 1<br>Fluorouracil 600 mg/m$^2$ i.v., day 1<br>Repeat cycle every 21 days |
| NFL | Mitoxentrone 12 mg/m$^2$ i.v., day 1<br>Fluorouracill 350 mg/m$^2$ i.v., days 1-3, after Leucovorin<br>Leucovorin 300 mg i.v., over 1 hour, days 1-3<br>OR<br>Mitoxentrone 10 mg/m$^2$ i.v., day 1<br>Fluorouracil 1,000 mg/m$^2$/d Cl, days 1-3, after leucovorin<br>Leucorvorin 100 mg/m$^2$ i.v., over 15 minutes, days 1-3<br>Repeat cycle every 21 days |
| Sequential Dox-CFM | Doxorubicin 75 mg/m$^2$ i.v., every 21 days, for 4 cycles followed by 21- or 280 day CMF for 8 cycles |
| VATH | Vinblastine 4.5 mg/m$^2$ i.v., day 1<br>Doxorubicin 4.5 mg/m$^2$ i.v., day 1<br>Thlotepa 12 mg/m$^2$ i.v., day 1<br>Fluoxymesterone 20 or 30 mg/d PO<br>Repeat cycle every 21 days |
| Vinorelbine Doxorubicin | Vinorelbine 25 mg/m$^2$ i.v., days 1, 8<br>Doxorubicin 50 mg/m$^2$ i.v., day 1<br>Repeat cycle every 21 days |
| | Single-Agent Regimens |
| Regimens | Chemotherapeutic Agent(s) |
| Anastrozole | Anastrozole 1 mg/d PO |
| Capecitabine | Capecitabine 1,250 mg/m$^2$ PO bid, days 1-14<br>Repeat cycle every 21 days |
| CFM (CNF, FNC) | Cyclophosphamide 600 mg/m$^2$ i.v., day 1<br>Fluorouracil 600 mg/m$^2$ i.v., day 1<br>Mitoxentrone 12 mg/m$^2$ i.v., day 1<br>Repeat cycle every 21 days |
| Docetaxel | Docetaxel 60-100 mg/m$^2$ i.v, over 1 hour, every 21 days |
| Gemcitabine | Gemcitabine 725 mg/m$^2$ i.v, over 30 minutes weekly for 3 weeks, followed by 1 week rest<br>Repeat cycle every 28 days |
| Letrozole | Letrozole 2.5 mg/d PO |
| Megestrol | Megestrol 40 mg PO bid |
| Paciltaxel | Paciltaxel 250 mg/m$^2$ i.v, over 3 or 24 hours every 21 days<br>OR<br>Paciltaxel 175 mg/m$^2$ i.v., over 3 hours, every 21 days |

TABLE 7-continued

Breast Cancer Regimens

| Regimens | Chemotherapeutic Agent(s) |
|---|---|
| Tamoxifen | Tamoxifen 10 or 20 mg twice daily or 20 mg/d PO |
| Toremifene citrate | Toremifene citrate 60 mg/d PO |
| Vinorelbine | Vinorelbine 30 mg/m² i.v, every 7 days |

EXAMPLE 19

Prostrate cancer, particularly metastatic prostrate cancer will be treated with the present complexes, e.g., with $^{166}$Ho-DOTMP, in accord with the present method, employing the regimens listed on Table 8.

TABLE 8

Prostrate Cancer Regimens

| Regimen | Chemotherapeutic Agent(s) |
|---|---|
| | Combination Regimens |
| Estramustine | Estramustine 200 mg/m² PO, tid, days 1-42 |
| Vinblastine | Vinblastine 4 mg/m² i.v., weekly for 6 weeks, begin day 1<br>Repeat cycle every 8 weeks |
| FL | Flutamide 250 mg PO, tid<br>WITH<br>Leuprolide acetate 1 mg/d SQ<br>OR<br>Leuprolide acetate depot 7.5 mg IM, every 28 days i.v., day 1 |
| FZ | Flutamide 250 mg PO, tid<br>WITH<br>Goserelin acetate 3.6 mg implant SQ, every 28 days<br>OR<br>Goserelin acetate 10.8 mg implant SQ every 12 weeks<br>Begin regimen 2 months prior to radiotherapy |
| Mitoxantrone | Mitoxantrone 12 mg/m² i.v., day 1 |
| Prednisone | Prednisone 5 mg PO, bid<br>Repeat cycle every 21 days |
| No Known Acronym | Bloatutamide 50 mg/d PO<br>WITH<br>Leuprolide acetate depot 7.5 mg IM, every 28 days<br>OR<br>Goserelin acetate 3.6 mg implant SQ, every 28 days |
| PE | Paciltaxel 120 mg/m² by 96-hour i.v. infusion, days 1-4<br>Estramustine 600 mg/d PO, qd, 24 hours before paciltaxel<br>Repeat cycle every 21 days |
| | Single Regimens |
| Regimen | Chemotherapeutic Agent(s) |
| Estramustine | Estramustine 14 mg/kg/d PO, in 3 or 4 divided doses |
| Goserelin | Goserelin acetate implant 3.6 mg implant SQ 8 weeks before radiotherapy, followed by 28 days by 10.8 mg implant SQ, every 12 weeks |
| Nilutamide | Nilutamide 300 mg PO, days 1-30, then 150 mg PO/d in combination with surgical castration; begin on same day or day after castration |
| Prednisone | Prednisone 5 mg PO, bid |

EXAMPLE 20

Treatment of Multiple Myeloma

Multiple myeloma will be treated with the present complexes, e.g., with $^{166}$Ho-DOTMP, in accord with the present method, employing the regimens listed on Table 9.

TABLE 9

Multiple Myeloma Regimens.

| Regimen | Chemotherapeutic Agent(s) |
|---|---|
| | Combination Regimens |
| M2 | Vincristine 0.03 mg/kg i.v., day 1<br>Carmustine 0.5-1 mg/kg i.v., day 1<br>Cyclophosphamide 10 mg/kg i.v., day 1<br>Melphalan 0.25 mg/kg PO, days 1-4<br>OR<br>Melphalan 0.1 mg/kg PO, days 1-7 or 1-10<br>Prednisone 1 mg/kg/d PO, days 1-7<br>Repeat cycle every 35-42 days |
| MP | Melphalan 8-10 mg/m² PO, days 1-4<br>Prednisone 60 mg/m² PO, days 1-4<br>Repeat cycle every 28-42 days |
| VBMCP | Vincristine 1.2 mg/m² i.v., day 1<br>Carmustine 20 mg/m² i.v., day 1<br>Melphalan 8 mg/m² PO, days 1-4<br>Cyclophosphamide 400 mg/m² i.v., day 1<br>Prednisone 40 mg/m² PO, days 1-7 all cycles, and 20 mg/m² PO, days 8-14 first 3 cycles only<br>Repeat cycle every 35 days |
| | Single-Agent Regimens |
| Dexamethasone | Dexamethasone 20 mg/m² PO, for 4 days beginning on days 1-4, 9-12 and 17-20<br>Repeat cycle every 14 days |
| Interferon alfa-2b | Interferon alfa-2b 2 million units/m² SQ 3 times a week for maintenance therapy in selected patients with significant response to initial chemotherapy treatment |
| Melphalan | Melphalan 90-140 mg/m² i.v.<br>Administer one cycle |

The invention has been described with reference to various specific and preferred embodiments and techniques. However, it should be understood that many variations and modifications may be made while remaining within the spirit and scope of the invention.

All patents, patent applications, and literature cited in the specification are hereby incorporated by reference in their entirety. In the case of any inconsistencies, the present disclosure, including any definitions therein will prevail.

The invention claimed is:

1. A therapeutic method for treating leukemia comprising:
   (a) hydrating a leukemia patient;
   (b) parenterally administering a dose of about 400-4000 mCi 153 Sm-EDTMP to said patient; and
   (c) administering a dose of melphalan, bisulfan, cyclophosphamide or a combination thereof, to said patient.

2. The method of claim 1 wherein the patient is refractory to treatment, or in relapse after treatment with chemotherapy and/or total body irradiation.

3. The method of claim 1 wherein about 460-1600 mCi 153 Sm-EDTMP is delivered in step (c).

4. The method of claim 1 wherein about 30-50 Gy of radiation are delivered in the bone marrow of the patient.

5. The method of claim 1 wherein the leukemia is myeloid leukemia.

6. A therapeutic method for treating a bone-associated cancer in a human patient comprising:
   (a) parenterally administering a dose of about 400-4000 mCi of a first chemotherapeutic agent that is 153 Sm-EDTMP; and (b) administering a dose of a second chemotherapeutic agent to said patients, wherein steps (a) and/or (b) are effective to suppress the bone marrow of a human patient.

7. The method of claim 6 wherein the patient is refractory to treatment of in relapse after treatment with chemotherapy and/or total body irradiation.

8. The method of claim 6 wherein the patient is hydrated prior to, during and/or after step (a).

9. The method of claim 6 wherein the bone associated cancer is prostate cancer or breast cancer that has metastasized to the bone.

10. The method of claim 6 wherein about 460-1600 mCi is administered in step (a).

11. The method of claim 6 herein the dose of 153 Sm-EDTMP is delivered by intravenous infusion or injection in an aqueous vehicle comprising an effective antiradiolytic amount of a pharmaceutically acceptable radioprotectant.

12. The method of claim 11 wherein the radioprotectant is an ascorbate or gentistic acid.

13. The method of claim 12 wherein the ascorbate is ascorbic acid at a concentration of about 35-75 mg/ml.

14. The method of claim 6 wherein the dose delivers about 30-40 Gy of radiation to the bone marrow of the patient.

15. The method of claim 6 wherein the dose delivers about 15-30 Gy of radiation to the bone marrow of the patient.

16. The method of claim 6 wherein about 140-200 mg/m2 of melphalan is administered.

* * * * *

UNITED STATES PATENT AND TRADEMARK OFFICE
CERTIFICATE OF CORRECTION

PATENT NO. : 7,378,077 B2 Page 1 of 1
APPLICATION NO. : 11/485183
DATED : May 27, 2008
INVENTOR(S) : Fritzberg et al.

It is certified that error appears in the above-identified patent and that said Letters Patent is hereby corrected as shown below:

In column 12, lines 66-67, delete "$^{66}$Ho-DOTMP," and insert -- $^{166}$Ho-DOTMP, --, therefor.

In column 33, line 15, in Claim 11, delete "herein" and insert -- wherein --, therefor.

Signed and Sealed this

Twelfth Day of August, 2008

JON W. DUDAS
*Director of the United States Patent and Trademark Office*